(12) United States Patent
Braddock et al.

(10) Patent No.: US 6,689,758 B1
(45) Date of Patent: Feb. 10, 2004

(54) GENE THERAPY METHOD

(75) Inventors: Martin Braddock, Loughborough (GB); Callum Jeffrey Campbell, Cambridge (GB); Jean-Luc Schwachtgen, Munich (DE)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/701,749

(22) PCT Filed: Jun. 2, 1999

(86) PCT No.: PCT/GB99/01722

§ 371 (c)(1),
(2), (4) Date: Jan. 29, 2001

(87) PCT Pub. No.: WO99/62561

PCT Pub. Date: Dec. 9, 1999

(30) Foreign Application Priority Data

| Jun. 2, 1998 | (GB) | 9811836 |
| Jul. 11, 1998 | (GB) | 9815035 |
| Sep. 12, 1998 | (GB) | 9819846 |
| Dec. 23, 1998 | (GB) | 9828578 |

(51) Int. Cl.[7] ................................................. A61K 48/00
(52) U.S. Cl. ...................... 514/44; 424/93.2; 424/93.21
(58) Field of Search .......................... 514/44; 424/93.2, 424/93.21

(56) References Cited

U.S. PATENT DOCUMENTS 5,206,152 A   4/1993   Sukhatme .................. 435/69.1

FOREIGN PATENT DOCUMENTS

| WO | 94/23030 | 10/1994 |
| WO | 97/32979 | 9/1997 |

OTHER PUBLICATIONS

Deonarain; Ligand–targeted receptor–mediated vectors for gene delivery, 1998, Exp. Opin. Ther. Patents 8: 53–69.*
Crystal; Transfer of Genes to Humans: Early Lessons and Obstacles to Success, 1995, Science, vol. 270: 404–410.*
Verma et.al.; Gene therapy–promises, problems and prospects, 1997, Nature, vol. 389: 239–242.*
Orkin et al.; Report and Recommendations of the Panel to Assess the NIH Investment in Research on Gene Therapy, issued by The US Natl. Inst. of Health, 1995.*
Khachigian L M et al: "Egr–1–induced endothelial gene expression: a common theme in vascular injury." Science, (Mar. 1996) 271 (5254) 1427–31.
Schwachtgen Jean–Luc et al: "Fluid shear stress activation of egr–1 transcription in cultured human endothelial and epithelial cells is mediated via the extracellular signal–related kinase 1/2 mitogen–activated protein kinase pathway." Journal of Clinical Investigation Jun. 1, 1998, vol. 101, No. 11, (Jun. 1998) pp. 2540–2549.
Sakamoto K M et al.: "5' Upsteam Sequence and Genomic Sructure of the Human Primary Response Gene EGR–1–TIS8" Oncogene 1991, vol. 6, No. 5, 1991, pp. 867–872.
Janssen–Timmen U et al.: "Structure, chromosome mapping and regulation of the mouse zinc–finger gene Krox–24; evidence for a common regulatory pathway for immediate–early serum–response genes." Gene, (Aug. 1989) 80 (2) 325–36.
Suggs S V et al.:"cDNA sequence of the human cellular early growth response gene Egr–1." Nucleic Acids Research, (Jul. 1990) 18 (14) 4283.

* cited by examiner

Primary Examiner—Scott D. Priebe
(74) Attorney, Agent, or Firm—Michael M. Conger

(57) ABSTRACT

The invention relates to the use of an Egr-1 transcription factor polypeptide or a biologically active fragment thereof, and to nucleic acid molecules encoding such polypeptides, in the manufacture of a medicament for the treatment of wounds in a mammal, including human. In addition, it relates to a sequence that is believed to include important regions involved in the transcription of the transcription factor Egr-1 in humans and in the regulation thereof. This sequence can be used to design appropriate nucleic acid molecules and vectors that can be used in the treatment of wounds, as well as in other treatment.

3 Claims, 30 Drawing Sheets

FIG.1a
VEGF expression
Day 0
Gold - DNA  Gold + Egr-1 DNA 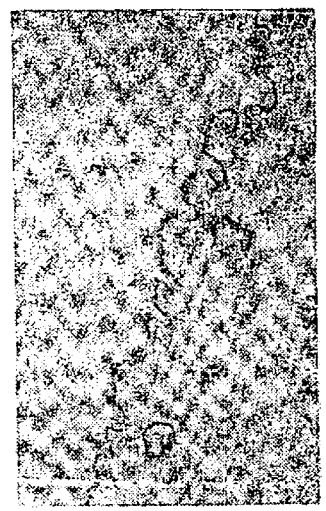
Day 1
Gold - DNA  Gold + Egr-1 DNA 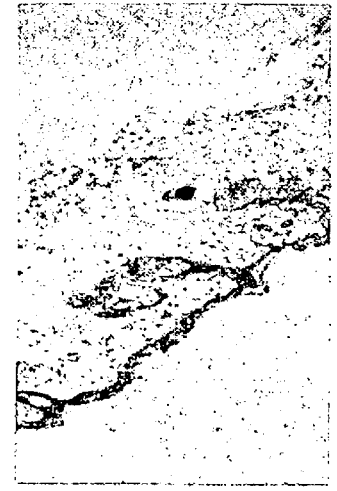

FIG.1b
VEGF expression
Day 2
Gold - DNA
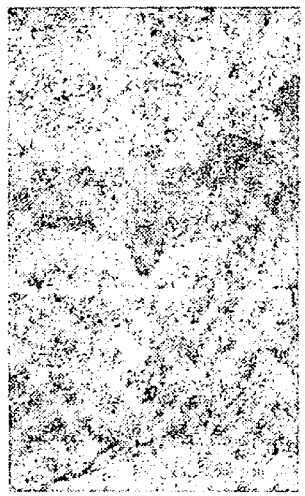
Gold + Egr-1 DNA
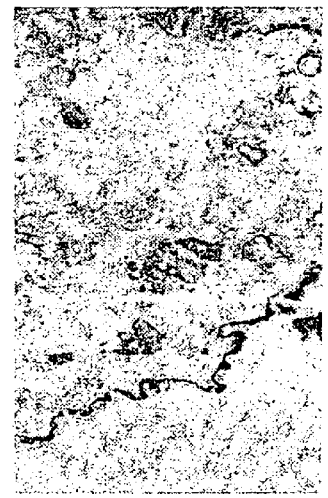
Day 6
Gold - DNA
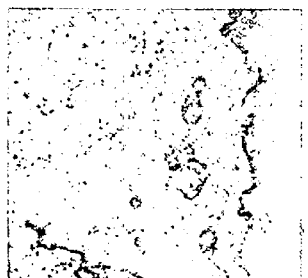
Gold + Egr-1 DNA

FIG.1c
TGF-$\beta_1$ expression
Day 0
Gold - DNA
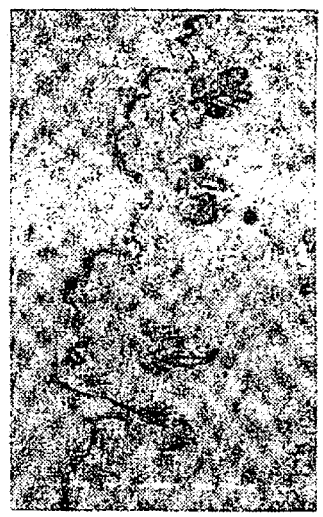
Gold + Egr-1 DNA
Day 1
Gold - DNA
Gold + Egr-1 DNA

TGF-$\beta_1$ expression        FIG.1d
Day 2
Gold - DNA                    Gold + Egr-1 DNA
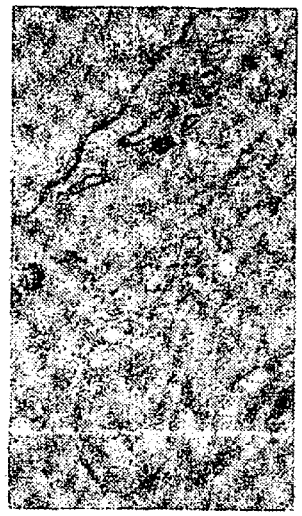          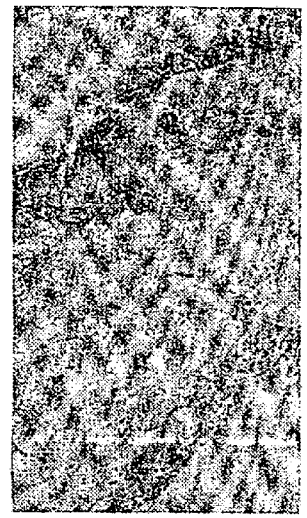
Day 6
Gold - DNA                    Gold + Egr-1 DNA
          

PDGFα expression
FIG.1e
Day 0
Gold - DNA 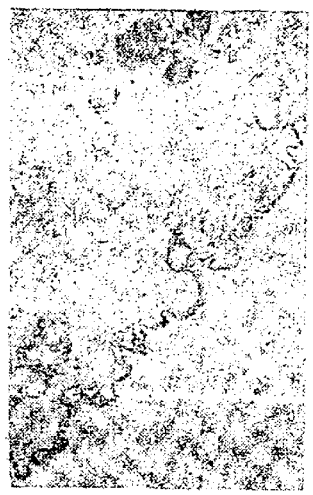 Gold + Egr-1 DNA 
Day 1
Gold - DNA  Gold + Egr-1 DNA 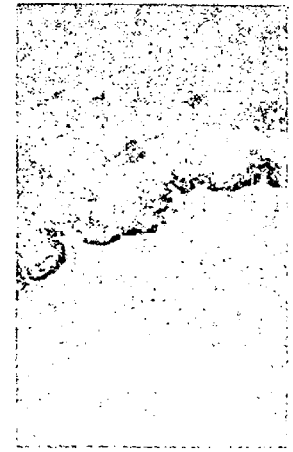

FIG.1f
PDGFα expression
Day 2
Gold - DNA
Gold +Egr-1 DNA
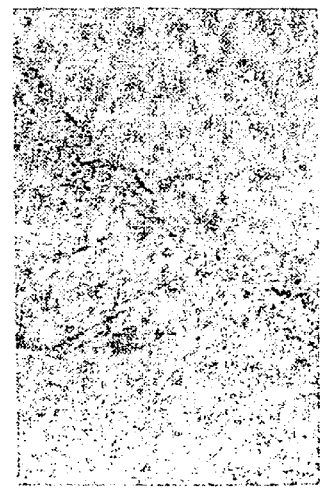

Effect of Egr-1 on rat excisional wound contraction

Effect of Egr-1 DNA transfection on the histology of healing rat excisional wounds Effect of Egr-1 on collagen deposition in rat excisional wounds Effect of Egr-1 on the angiogenic profile in rat excisional wounds using vWF immunostaining.

Optimisation of Lipid:DNA ratio (v/w) for transfection of pGL3 luciferase control plasmid into the angiogenesis co-culture system using Mirus TransIT (Cambridge Biosciences).

Effect of Egr-1 on angiogenesis. CMV-Egr-1 DNA was transfected into the co-culture as described using Mirus Transit. Shown is Egr-1 over a titration range, non-treated, and effects of an agonsist (VEGF protein) and antagonist (suramin).

Fig. 4a

For each treatment at each time point there are were three samples as shown. Each sample represents cells pooled from three replicate experiments.

Sample Identification

| Sample No. | Treatment | Sample No. | Treatment |
|---|---|---|---|
| 1 | Load 24 hrs | 43 | Solute control 0 hrs |
| 2 | ↓ | 44 | ↓ |
| 3 | ↓ | 45 | ↓ |
| 4 | Control 24 hrs | 46 | Positive control 0 hrs |
| 5 | ↓ | 47 | ↓ |
| 6 | ↓ | 48 | ↓ |
| 7 | Solute control 24 hrs | 49 | Load 2 hrs |
| 8 | ↓ | 50 | ↓ |
| 9 | ↓ | 51 | ↓ |
| 10 | Positive control 24 hrs | 52 | Control 2 hrs |
| 11 | ↓ | 53 | ↓ |
| 12 | ↓ | 54 | ↓ |
| 13 | Load 48 hrs | 55 | Solute control 2 hrs |
| 14 | ↓ | 56 | ↓ |
| 15 | ↓ | 57 | ↓ |
| 16 | Control 48 hrs | 58 | Positive control 2 hrs |
| 17 | ↓ | 59 | ↓ |
| 18 | ↓ | 60 | ↓ |
| 19 | Solute control 48 hrs | 61 | Load 4 hrs |
| 20 | ↓ | 62 | ↓ |
| 21 | ↓ | 63 | ↓ |
| 22 | Positive control 48 hrs | 64 | Control 4 hrs |
| 23 | ↓ | 65 | ↓ |
| 24 | ↓ | 66 | ↓ |
| 25 | Load 72 hours | 67 | Solute control 4 hrs |
| 26 | ↓ | 68 | ↓ |
| 27 | ↓ | 69 | ↓ |
| 28 | Control 72 hours | 70 | Positive control 4 hrs |
| 29 | ↓ | 71 | ↓ |
| 30 | ↓ | 72 | ↓ |
| 31 | Solute control 72 hrs | 73 | Load 6 hrs |
| 32 | ↓ | 74 | ↓ |
| 33 | ↓ | 75 | ↓ |
| 34 | Positive control 72 hrs | 76 | Control 6 hrs |
| 35 | ↓ | 77 | ↓ |
| 36 | ↓ | 78 | ↓ |
| 37 | Load 0 hrs | 79 | Solute control 6 hrs |
| 38 | ↓ | 80 | ↓ |
| 39 | ↓ | 81 | ↓ |
| 40 | Control 0 hrs | 82 | Positive control 6 hrs |
| 41 | ↓ | 83 | ↓ |
| 42 | ↓ | 84 | ↓ |

Western blot analysis of Egr-1 protein in human TE85 bone cells exposed to load.

Arrow denotes Egr-1 protein. Lanes 1 and = positive controls, lane 3 = PMA control after 24 hrs. Lanes 4 to 8 inclusive represent loading for 2,4,6,24 and 48 hrs respectively and lanes 9 to 13 are the unloaded controls.

Fig. 4c
ELISA analysis of PDGF BB produced from human TE85 bone cells after exposure to load.
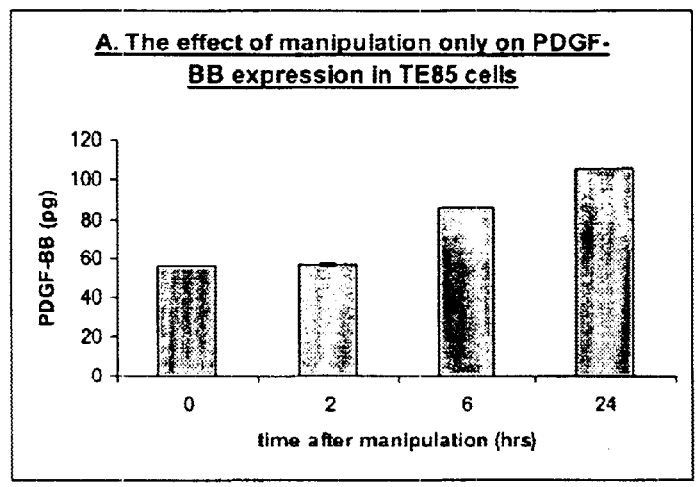
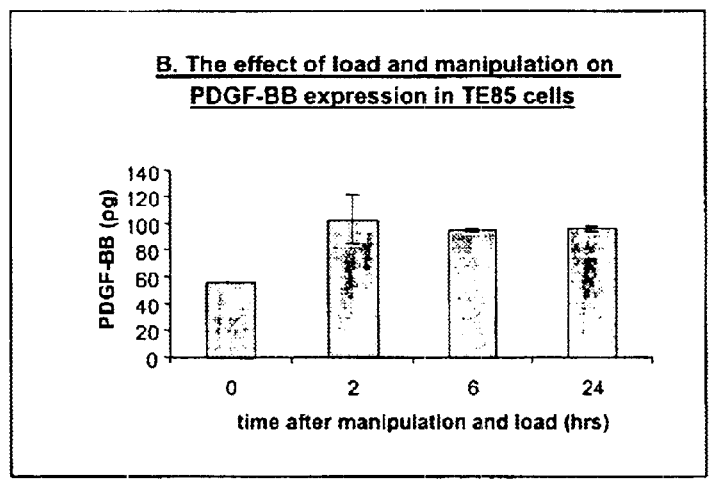

Fig. 4d
Detection of VEGF and TGF-β1 after transfection of CMV-TGF-β1 in ROS cells.
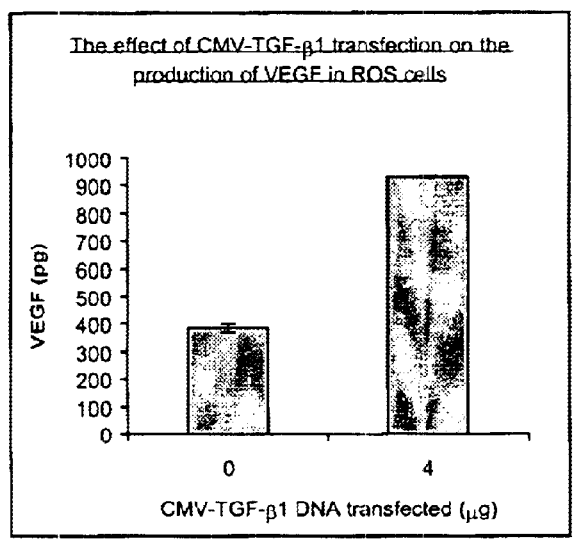
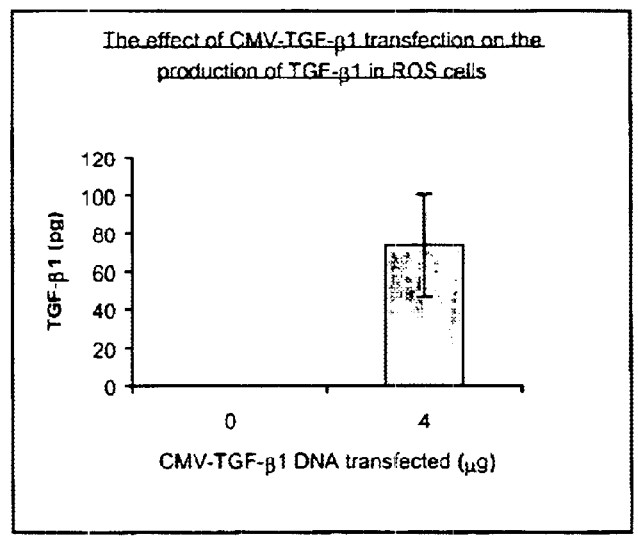

Fig. 4e
Detection of VEGF and TGF-β1 after transfection of CMV-TGF-β1 in MC3t3E1 cells.
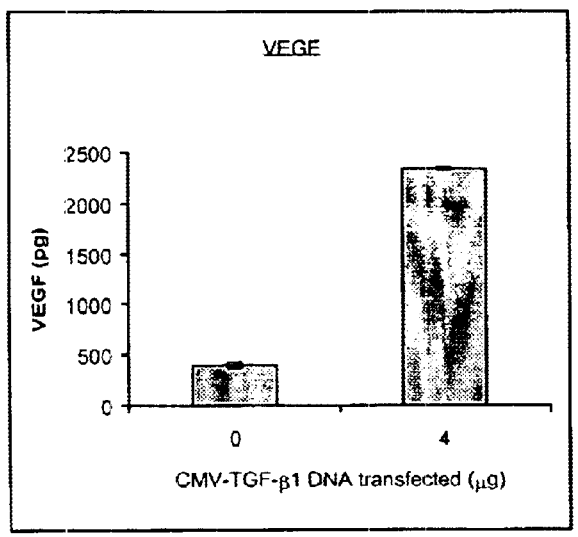
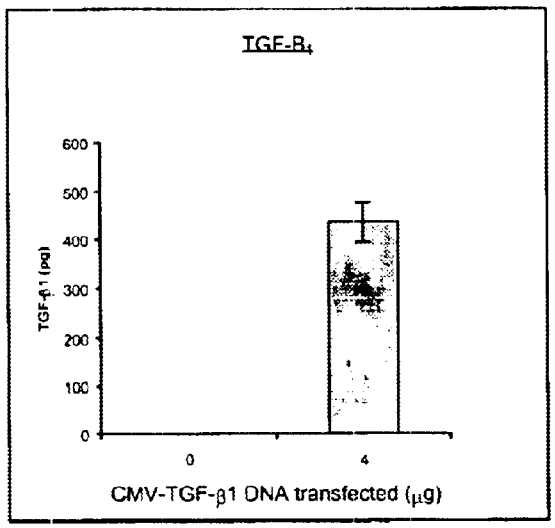

Fig. 5

Effect Of Egr-1 On Alkaline Phosphatase Levels In A Rodent Model Of Ectopic Bone Formation

|  | Control | DNA and BMP | DNA | BMP |
|---|---|---|---|---|
|  | N=10 sites | N=10 sites | N=10 sites | N=10 sites |
| Alkaline phosphate Median (IQR) | 0.48 (0.28, 0.55) | 0.90 (0.66, 1.57) | 1.30 (0.55, 2.03) | 0.63 (0.53, 1.0) |
| PNP median (IQR) | 5.90 (3.78, 11.26) | 17.45 (10.22, 22.23) | 18.11 (5.69, 37.73) | 15.89 (4.16, 27.76) |
|  | N=5 sites | N= 5 sites | N=5 sites | N=5 sites |
| Ca as %of dry weight Mean (SD) | 0.106 (0.035) | 0.098 (0.035) | 0.1060 (0.042) | 0.097 (0.032) |
| Ca as % of dry weight Median (IQR) | 0.09 (0.09, 0.13) | 0.08 (0.08, 0.125) | 0.09 (0.07, 0.15) | 0.07 (0.06, 0.10) |
| Collagen, median (IQR) | 0.91 (0.775, 1.455) | 1.24 (1.10, 1.45) | 0.99 (0.75, 1.23) | 0.87 (0.705, 1.50) |
| Bone formation | 0 | 1 site | 0 | 0 |

FIG.6a
Anti- Egr-1 antibody staining of human smooth muscle cells transfected with CMV Egr-1
 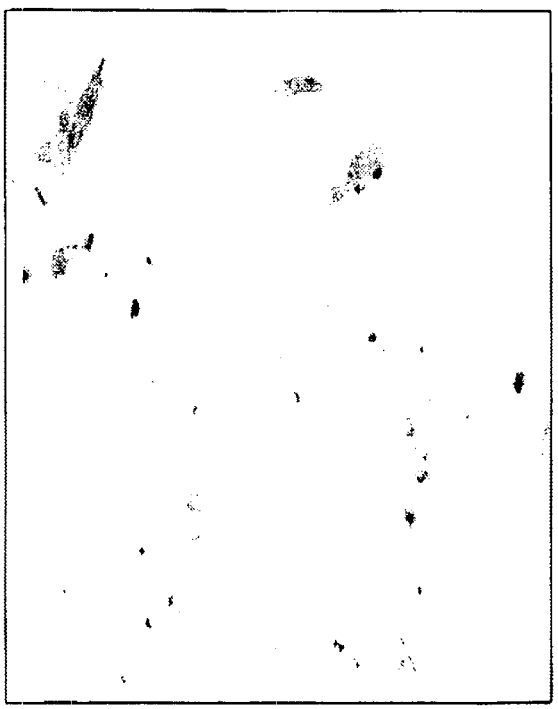
Test Mock

FIG.6b
Anti-Egr-1 antibody staining of porcine smooth muscle cells transfected with CMV Egr-1 DNA.
 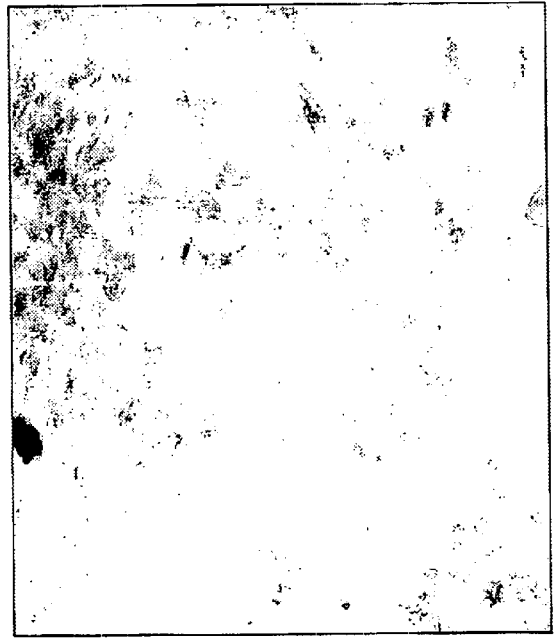
Test                                    Mock Optimisation of transfection of pGL3 luciferase control into human SMC by Fugene.

Optimisation of transfection of pGL3 luciferase control into porcine SMC by Fugene.

Activation of VEGF production/secretion by transfection of CMV-Egr-1 into human SMC.

Activation of HGF production/secretion by transfection of CMV-Egr-1 into human SMC.

Activation of PDGF production/secretion by transfection of CMV Egr-1 into human SMC.

Immunostaining of Egr-1 protein in vessel wall pre and post injury

Fig. 7

Wild type human egr-1 promoter

```
                                     Sp1                   cAMP RE             TPA RE
ON SEQ  CGGTTCGCTC TCACGGTCCC TGAGGTGGGC GGGCGGGCC. TGGAGGACAG CGATAGAACC CCGGCCCGAG
GW SEQ  CGGTTCGCTC TCACGGTCCC TGAGGTGGGC GGGCGGGCCC TGGATGACAG CGATAGAACC CCGGCCCGAG
            10         20         30         40         50         60         70
             EBS
ON SEQ  TCGCCCTCGC CCCCGCTCTG GGTCTGGGCT TCCCCAGCCT AGTTCACGCC TAGGAGCCGC CTGAGCAGCC
GW SEQ  TCGCCCTCGC CCCCGCTCTG GGTCTGGGCT TCCCCAGCCT AGTTCACGCC TAGGAGCCGC CTGAGCAGCC
            80         90        100        110        120        130        140
                                              Sp1
ON SEQ  GCGC.CA.AG CGCCACACGC CACGAGCCCT CCCCGCCTGG GCGTCCCCGG ATCCCGCGAG CGCTCGGGCT
GW SEQ  GCGCGCCCAG CGCCACACGC CACGAGCCCT CCCCGCCTGG GCGTCCCCGG ATCCCGCGAG CGCTCGGGCT
           150        160        170        180        190        200        210
                                                                             SRE5
ON SEQ  CCCGGCTTGG AACCAGGGAG GAGGGAGGGA GCGAGGGAGC AACCAGCT.C GGACC.GGAAA TGCCATATA
GW SEQ  CCCGGCTTGG AACCAGGGAG GAGGGAGGGA GCGAGGGAGC AACCAGCTGC G.ACCCGGAA ATGCCATATA
           220        230        240        250        260        270        280
         SRE5                       SRE4              SRE3
ON SEQ  GAGCAGGA AGGATCCCCC GCCGGAACAA CCCTTATTTG GGCAGGACCT TATTTGGAGT GGCCGGATAT
GW SEQ  AGAAGCAGGA AGGATCCCCC GCCGGAACAA CCGTTATTTG GGCAGGACCT TATTTGGAGT GGCCCGATAT
           290        300        310        320        330        340        350

ON SEQ  GGCCCGGC.G CTTCCGCCTC TGGGAGGAGG GAAGAAGGCG GAGGGAGGGG CAACGCGGGA ACTCCGGAGC
GW SEQ  GGCCCGGCCG CTTCCGGCTC TGGGAGGAGG GAAGAAGGCG GAGGGAGGGG CAACGCGGGA ACTCCGGAGC
           360        370        380        390        400        410        420

ON SEQ  TGC.CGG.TC CCGGAGGCCC CGGCGGCGGC TAGAGCTCTA GGCTTCCCCG AAGC.TGGGC GCCTGGGATG
GW SEQ  TGCGCGGGTC CCGGAGGCCC CGGCGGCGGC TAGAGCTCTA GGCTTCCCCG AAGCCTGGGC GCCTGGGATG
           430        440        450        460        470        480        490
                                                                             cAMP RE
ON SEQ  CGGGC.CGGG C.CGGGCCCT AGGGTGCAGG ATGGAGGTGC CGGGCGCTGT CGGATGGGGG GCTTCACGTC
GW SEQ  CGGGCGCGGG CGCGGGCCCT AGGGTGCAGG ATGGAGGTGC CGGGCGCTGT CGGATGGGGG GCTTCACGTC
           500        510        520        530        540        550        560
                              SRE2       SRE1
ON SEQ  ACTCCGGGTC CTCCC..CCG GTCCTGCCAT ATTAGGGCTT C.TGCTTCCC ATATATG.CC ATGTACGTCA
GW SEQ  ACTCCGGGTC CTCCCGGCCG GTCCTGCCAT ATTAGGGCTT CCTGCTTCCC ATATATGGCC ATGTACGTCA
           570        580        590        600        610        620        630
                                             TATA
ON SEQ  CGACGGAGGC GGACCCGTGC CGTTCCAGAC CCTTCAAATA GAGGCGGATC CGGGGAGTCG CGAGAGATCC
GW SEQ  CGACGGAGGC GGACCCGTGC CGTTCCAGAC CCTTCAAATA GAGGCGGATC CGGGGAGTCG CGAGAGATCC
           640        650        660        670        680        690        700

ON SEQ  AGC
GW SEQ  AGC
           713
```

Fig. 8

Mutant human egr-1 promoter

```
                                        Sp1                cAMP RE              TPA RE
CGGTTCGCTC TCACGGTCCC TGAGGTGGGC GGCGGGCCC TGGATGACAG CGATAGAACC CCGGCCCGAC
    10         20         30         40         50         60         70

EBS
TCGCCCTCGG TATCGCTCTG GGTCTGGGCT TCCCCAGCCT AGTTCACGCC TAGGAGCCGC CTGAGCAGCC
    80         90        100        110        120        130        140

Sp1
GCGCGCCCAG CGCCACACGC CACGAGCCCT CGCCGCCGTGG GCGTCCCCGG ATCCCGCGAG CGCTCGGGCT
   150        160        170        180        190        200        210

SRE5
CCCGGCTTGG AACCAGGGAG GAGGGAGGGA GCGAGGGAGC AACCAGCTGC G.ACCCGGAA ATGCCATATA
   220        230        240        250        260        270        280

SRE5                        SRE4                  SRE3
AGAAGCAGGA AGGATCCCCC GCCGGAAGAA CCGTTATTTG GGCAGCACCT TATTTGGAGT GGCCGGATAT
   290        300        310        320        330        340        350

GGCCCGGCCG CTTCCGGCTC TGGGAGGAGG GAAGAAGGCG GAGGGAGGGG CAACGCGGGA ACTCCGGAGC
   360        370        380        390        400        410        420

TGCGCGGGTC CCGGAGGCCC CGGCGGCGGC TAGAGCTCTA GGCTTCCCCG AAGCCTGGGC GCCTGGGATG
   430        440        450        460        470        480        490 cAMP RE
CGGGCGCGGG CGCGGGCCCT AGGGTGCAGG ATGGAGGTGC CGGGCGCTGT CGGATGGGGG GCTTCACGTG
   500        510        520        530        540        550        560

SRE2       SRE1
ACTCCGGGTC CTCCCGGCCG GTCCTGCCAT ATTAGGGCTT CCTGCTTCCC ATATATGGCC ATGTACGTCA
   570        580        590        600        610        620        630

TATA
CGACGGAGGC GGACCCGTGC CGTTCCAGAC CCTTCAAATA GAGGCGGATC CGGGGAGTCG CGAGAGATCC
   640        650        660        670        680        690        700

AGC
713
```

Fig. 9

Published 5' Upstream Sequence Of Mouse Egr-1 Gene

```
-935                                                                          -876
ACGGAGGGAA  TAGCCTTTCG  ATTCTGGGTG  GTGCATTGGA  AGCCCCAGGC  TCTAAAACCC
-875                                                                          -816
CCAACCTACT  GACTGGTGGC  CGAGTATGCA  CCCGACTGCT  AGCTAGGCAG  TGTCCCAAGA
-815                                                                          -756
ACCAGTAGCC  AAATGTCTTG  GCCTCAGTTT  TCCCGGTGAC  ACCTGGAAAG  TGACCCTGCC
-755                                                                          -696
ATTAGTAGAG  GCTCAGGTCA  GGGCCCCGCC  TCTCCTGGGC  GGCCTCTGCC  CTAGCCCGCC
-695                                                                          -636
CTGCCGCTCC  TCCTCTCCGC  AGGCTCGCTC  CCACGGTCCC  CGAGGTGGGC  GGGTGAGCCC
-635                                                                          -576
AGGATGACGG  CTGTAGAACC  CCGGCCTGAC  TCGCCCTCGC  CCCCGCGCCG  GGCCTGGGCT
-575                                                                          -516
TCCCTAGCCC  AGCTCGCACC  CGGGGGCCGT  CGGAGCCGCC  GCGCGCCCAG  CTCTACGCGC
-515                                                                          -456
CTGGCCCTCC  CCACGCGGGC  GTCCCCGACT  CCCGCGCGCG  CTCAGGCTCC  CAGTTGGGAA
-455                                                                          -396
CCAAGGAGGG  GGAGGATGGG  GGGGGGGGTG  TGCGCCGACC  CGGAAACGCC  ATATAAGGAG
-395                                                                          -336
CAGGAAGGAT  CCCCCGCCGG  AACAGACCTT  ATTTGGGCAG  CGCCTTATAT  GGAGTGGCCC
-335                                                                          -276
AATATGGCCC  TGCCGCTTCC  GGCTCTGGGA  GGAGGGGCGA  GCGGGGGTTG  GGGCGGGGGC
-275                                                                          -216
AAGCTGGGAA  CTCCAGGCGC  CTGGCCCGGG  AGGCCACTGC  TGCTGTTCCA  ATACTAGGCT
-215                                                                          -156
TTCCAGGAGC  CTGAGCGCTC  GCGATGCCGG  AGCGGGTCGC  AGGGTGGAGG  TGCCCACCAC
-155                                                                          -96
TCTTGGATGG  GAGGGCTTCA  CGTCACTCCG  GGTCCTCCCG  GCCGGTCCTT  CCATATTAGG
-95                                                                           -36
GCTTCCTGCT  TCCCATATAT  GGCCATGTAC  GTCACGGCGG  AGGCGGGCCC  GTGCTGTTCC
-35                                                                           +25
AGACCCTTGA  AATAGAGGCC  GATTCGGGGA  GTCGCGAGAG  ATCCCAGCGC  GCAGAACTTG
+26                                                                           +85
GGGAGCCGCC  GCCGCGATTC  GCCGCCGCCG  CCAGCTTCCG  CCGCCGCAAG  ATCGGCCCCT
+86                                                                           +145
GCCCCAGCCT  CCGCGGCAGC  CCTGCGTCCA  CCACGGGCCG  CGGCTACCGC  CAGCCTGGGG
+146                                                                          +205
GCCCACCTAC  ACTCCCCGCA  GTGTGCCCCT  GCACCCCGCA  TGTAACCCGG  CCAACCCCCG
+206                                                                          +265
GCGAGTGTGC  CCTCAGTAGC  TTCGGCCCCG  GGCTGCGCCC  ACCACCCAAC  ATCAGTTCTC
```

Fig. 10

Activation of SRE5 by transient transfection of pFA-MEK1.

|  | PSV40 (fold activation) | PSVSRE5 (fold activation) |
|---|---|---|
| PFA-dbd | 1 | 2.15 |
| PFA-MEK1 | 1.13 | 6.70 |

SEQUENCE LISTING

<160> NUMBER OF SEQ ID NOS: 8

<210> SEQ ID NO 1
<211> LENGTH: 1200
<212> TYPE: DNA
<213> ORGANISM: Mus sp.

<400> SEQUENCE: 1
acggagggaa tagcctttcg attctgggtg gtgcattgga agccccaggc tctaaaaccc      60
ccaacctact gactggtggc cgagtatgca cccgactgct agctaggcag tgtcccaaga     120

-continued

| | |
|---|---|
| accagtagcc aaatgtcttg gcctcagttt tcccggtgac acctggaaag tgaccctgcc | 180 |
| attagtagag gctcaggtca gggccccgcc tctcctgggc ggcctctgcc ctagcccgcc | 240 |
| ctgccgctcc tcctctccgc aggctcgctc ccacggtccc cgaggtgggc gggtgagccc | 300 |
| aggatgacgg ctgtagaacc ccggcctgac tcgccctcgc cccgcgccg gcctgggct | 360 |
| tccctagccc agctcgcacc cggggccgt cggagccgcc gcgcgcccag ctctacgcgc | 420 |
| ctggccctcc ccacgcgggc gtccccgact cccgcgcgcg ctcaggctcc cagttgggaa | 480 |
| ccaaggaggg ggaggatggg gggggggtg tgcgccgacc cggaaacgcc atataaggag | 540 |
| caggaaggat cccccgccgg aacagacctt atttgggcag cgccttatat ggagtggccc | 600 |
| aatatggccc tgccgcttcc ggctctggga ggaggggcga gcggggttg gggcgggggc | 660 |
| aagctgggaa ctccaggcgc ctggcccggg aggccactgc tgctgttcca atactaggct | 720 |
| ttccaggagc ctgagcgctc gcgatgccgg agcgggtcgc agggtggagg tgcccaccac | 780 |
| tcttggatgg gagggcttca cgtcactccg gtcctcccg gccggtcctt ccatattagg | 840 |
| gcttcctgct tcccatatat ggccatgtac gtcacggcgg aggcgggccc gtgctgttcc | 900 |
| agacccttga aatagaggcc gattcgggga gtcgcgagag atcccagcgc gcagaacttg | 960 |
| gggagccgcc gccgcgattc gccgccgccg ccagcttccg ccgccgcaag atcggcccct | 1020 |
| gccccagcct ccgcggcagc cctgcgtcca ccacgggccg cggctaccgc cagcctgggg | 1080 |
| gcccacctac actccccgca gtgtgcccct gcaccccgca tgtaacccgg ccaaccccccg | 1140 |
| gcgagtgtgc cctcagtagc ttcggccccg ggctgcgccc accacccaac atcagttctc | 1200 |

<210> SEQ ID NO 2
<211> LENGTH: 684
<212> TYPE: DNA
<213> ORGANISM: Homo sapiens

<400> SEQUENCE: 2

| | |
|---|---|
| cggttcgctc tcacggtccc tgaggtgggc gggcgggcct ggaggacagc gatagaaccc | 60 |
| cggcccgact cgccctcgcc cccgctctgg gtctgggctt cccagccta gttcacgcct | 120 |
| aggagccgcc tgagcagccg cgccaagcgc cacacgccac gagccctccc cgcctgggcg | 180 |
| tccccggatc ccgcgagcgc tcgggctccc ggcttggaac cagggaggag ggagggagcg | 240 |
| agggagcaac cagctcggac cggaatgcat atagagcagg aaggatcccc cgccggaaca | 300 |
| acccttattt gggcagcacc ttatttggag tggccggata tggcccggcg cttccgcctc | 360 |
| tgggaggagg gaagaaggcg gagggagggg caacgcggga actccggagc tgccggtccc | 420 |
| ggaggccccg gcgcggcta gagctctagg cttccccgaa gctgggcgcc tgggatgcgg | 480 |
| gccgggccgg gccctagggt gcaggatgga ggtgccgggc gctgtcggat gggggggcttc | 540 |
| acgtcactcc gggtcctccc ccgtcctgc catattaggg cttctgcttc ccatatatgc | 600 |
| catgtacgtc acgacggagg cggacccgtg ccgttccaga cccttcaaat agaggcggat | 660 |
| ccggggagtc gcgagagatc cagc | 684 |

<210> SEQ ID NO 3
<211> LENGTH: 702
<212> TYPE: DNA
<213> ORGANISM: Homo sapiens

<400> SEQUENCE: 3

| | |
|---|---|
| cggttcgctc tcacggtccc tgaggtgggc gggcgggccc tggatgacag cgatagaacc | 60 |
| ccggcccgac tcgccctcgc cccgctctg ggtctgggct tccccagcct agttcacgcc | 120 |

```
taggagccgc ctgagcagcc gcgcgcccag cgccacacgc cacgagccct ccccgcctgg    180
gcgtccccgg atcccgcgag cgctcgggct cccggcttgg aaccagggag gagggaggga    240
gcgagggagc aaccagctgc gacccggaaa tgccatataa gaagcaggaa ggatcccccg    300
ccggaacaac ccttatttgg gcagcacctt atttggagtg gcccgatatg gcccggccgc    360
ttccggctct gggaggaggg aagaaggcgg agggaggggc aacgcgggaa ctccggagct    420
gcgcgggtcc cggaggcccc ggcggcggct agagctctag gcttccccga agcctgggcg    480
cctgggatgc gggcgcgggc gcgggcccta gggtgcagga tggaggtgcc gggcgctgtc    540
ggatgggggg cttcacgtca ctccgggtcc tcccggccgg tcctgccata ttagggcttc    600
ctgcttccca tatatggcca tgtacgtcac gacggaggcg gacccgtgcc gttccagacc    660
cttcaaatag aggcggatcc ggggagtcgc gagagatcca gc    702
```

<210> SEQ ID NO 4
<211> LENGTH: 702
<212> TYPE: DNA
<213> ORGANISM: Homo sapiens

<400> SEQUENCE: 4

```
cggttcgctc tcacggtccc tgaggtgggc gggcgggccc tggatgacag cgatagaacc     60
ccggcccgac tcgccctcgc tatcgctctg ggtctgggct tccccagcct agttcacgcc    120
taggagccgc ctgagcagcc gcgcgcccag cgccacacgc cacgagccct ccccgcctgg    180
gcgtccccgg atcccgcgag cgctcgggct cccggcttgg aaccagggag gagggaggga    240
gcgagggagc aaccagctgc gacccggaaa tgccatataa gaagcaggaa ggatcccccg    300
ccggaacaac ccttatttgg gcagcacctt atttggagtg gcccgatatg gcccggccgc    360
ttccggctct gggaggaggg aagaaggcgg agggaggggc aacgcgggaa ctccggagct    420
gcgcgggtcc cggaggcccc ggcggcggct agagctctag gcttccccga agcctgggcg    480
cctgggatgc gggcgcgggc gcgggcccta gggtgcagga tggaggtgcc gggcgctgtc    540
ggatgggggg cttcacgtca ctccgggtcc tcccggccgg tcctgccata ttagggcttc    600
ctgcttccca tatatggcca tgtacgtcac gacggaggcg gacccgtgcc gttccagacc    660
cttcaaatag aggcggatcc ggggagtcgc gagagatcca gc    702
```

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 5

```
ggccacgcgt cgtcggttcg ctctcacggt ccc    33
```

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 6

```
gcagctcgag gctggatctc tcgcgactcc    30
```

<210> SEQ ID NO 7

```
-continued

<211> LENGTH: 52
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
aggctgcgac ccggaaatgc catataagaa gcaggaagga tccccccgcc gg            52

<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
agccggcggg gggatccttc ctgcttctta tatggcattt ccgggtcgca gc            52
```

GENE THERAPY METHOD

This application is a national phase application of International Patent Appln: No. PCT/GB99/01722 filed Jun. 2, 1999, which designated the US.

This invention relates to the use of gene therapy techniques in wound healing and associated conditions. More particularly, it relates to a new use of polynucleotides encoding early growth response-1 (Egr-1) transcription factor in the treatment of wounds, wound healing and associated conditions such as in the treatment of dermal ulcers arising from ischaemia and neuropathy associated with diabetes, peripheral arterial occlusive disease, deep vein thrombosis, chronic venous insufficiency and pressure sores, reduction of post-operative scarring associated with, for example, cataracts, skin graft procedures burns, psoriasis, acceleration of tissue remodelling and regeneration; hard tissue repair, for example bone; soft tissue repair, for example tendon, ligament, muscle, the promotion of angiogenesis, re-endothelialisation following percutaneous trans-luminal coronary angioplasty, inhibition of left ventricular cardiac hypertrophy, modulation of vessel wall calcification and the promotion of neuroregeneration.

Further utilities may include inhibition of fibrotic conditions, for example, pulmonary and liver fibrosis, and prevention of alopecia.

The invention also relates to the transcription of Egr-1 and to the regulation thereof.

The healing of skin involves a wide range of cellular, molecular, physiological and biochemical events. During the healing process, cells migrate to wound sites where they proliferate and synthesise extracellular matrix components in order to reconstitute a tissue closely similar to the uninjured original. This activity is regulated by mediators secreted from the wound border cells such as platelet-derived growth factor (PDGF), epidermal growth factor (EGF), transforming growth factor (TGF) beta and other cytokines. Beneficial effects of these agents on cells has been demonstrated both in vitro and in vivo (reviewed by Moulin, Eur. J. Cell Biol. 68; 1–7, 1995), including benefit of administering PDGF in rat models of diabetes (Brown et al J.Surg. Res. 56; 562–570, 1994).

Over the last five years numerous growth factors have been shown to accelerate cell proliferation in vitro and to promote wound healing in animal models. TGF beta has received the greatest attention in the context of wound repair as it promotes cell proliferation, differentiation and matrix production. TGF beta administered either topically or systemically accelerates the rate of cutaneous wound repair in animal models. (Ashcroft et al Nature Medicine, 3; 1209–1215, 1997; Sporn and Roberts J. Cell Biol. 119; 1017–1021, 1997; Beck et al J. Clin. Invest. 92; 2841–2849, 1993). Likewise PDGF has been reported to promote re-epithelialisation and revascularisation in ischemic tissue and diabetic animals (Uhl et al Langenbecks Archiv fur Chirurgie-Supplement-Kongressband 114; 705–708, 1997 and reviewed in Dirks and Bloemers Mol. Biol. Reports 22; 1–24, 1996).

The transcription factor Egr-1 is a potential regulator of over 30 genes and plays a role in growth, development and differentiation (reviewed in Liu et al Crit. Rev. Oncogenesis 7; 101–125, 1996; Khachigian and Collins Circ. Res. 81; 457–461, 1997). Egr-1 is induced upon injury to the vascular endothelium (e.g. Khachigian et al Science; 271; 1427–1431, 1996) and targets for transcriptional activation are numerous genes including epidermal growth factor (EGF), platelet-derived growth factor-A (PDGF-A), basic fibroblast growth factor (bFGF), induction of PDGF A, PDGF B, TGF beta, bFGF, uro-plasminogen activator (u-PA), tissue factor and insulin-like growth factor-2 (IGF-2).

The transcription complex that mediates vascular endothelial growth factor (VEGF) induction is dependent upon AP2 and not Egr-1 directly (Gille et al EMBO J 16; 750–759, 1997). However PDGF B directly upregulates VEGF expression (Finkenzeller Oncogene 15; 669–676, 1997). Transcription of VEGF mRNA is enhanced by a number of factors including PDGF B, bFGF, keratinocyte growth factor (KGF), EGF, tumpur necrosis factor (TNF) alpha and TGF beta1. VEGF has been to promote re-endothelialisation in the balloon injured artery. Data obtained in rabbits demonstrated a clear VEGF driven passivation of metallic stents effecting an inhibition of in-stent neo-intima formation, a decrease in the occurrence of thrombotic occlusion, an acceleration of re-endothelialisation of the prosthesis and an increase in vasomotor activity (van Belle, E. et al, Bichem. Biophys. Res. Comm., 235; 311–316, 1997; van Belle, E. et al, J. Am. Coll. Cardiol., 29; 1371–1379, 1997; Asahara, T., et al, Circulation, 94; 3291–3302, 1997). NIH approval for a pilot study of VEGF to promote re-endothelialisation in humans was granted in 1996. In addition, HGF has also been shown to promote re-endothelialisation following balloon angioplasty in a rat model of carotid artery injury (Nakamura et al, Abstract 1681, American Heart Association Meeting; Dallas, 1998). In animal models, VEGF-driven passivation of metallic stents has been shown to inhibit neo-intima formation, accelerate re-endothelialisation and increase vasomotor activity (Asahara et al Circulation; 94, 3291–3302.

VEGF expression has been reported in healing wounds and psoriatic skin, both conditions in which TGF alpha and its ligand the EGF receptor (EGFr) are upregulated. Expression of EGF induces Egr-1 (Iwami et al Am. J. Physiol. 270; H2100–2107, 1996; Fang et al Calcified Tissue International 57; 450–455, 1995; J. Neuroscience Res. 36; 58–65, 1993). There is at present anecdotal evidence that Egr-1 may activate the expression of inter-cellular adhesion molecule-1 (ICAM-1) in phorbol ester stimulated B lymphocytes (Maltzman et al Mol. Cell. Biol. 16; 2283–2294, 1996) and may activate the expression of TNF alpha by virtue of the presence of an Egr-1 binding site in the TNF alpha promoter (Kramer et al Biochim. Biophys. Acta 1219; 413–421, 1994). Finally, Egr-1 knock out mice are infertile and luteinizing hormone (LH) deficient (Lee et al, Science 273; 1219–1221, 1996) implying that the LH promoter may also be a target for Egr-1 activation.

Bone loading, mechanical stretch and fluid flow of osteoblast-like MC3T3E1 cells induces Egr-1 (Dolce et al Archs. Oral Biol. 41; 1101–1118, 1996; Ogata J. Cell Physiol. 170; 27–34, 1997) with concomitant activation of growth factors. Egr-1 expression predominates in the cartilage and bone of the developing mouse (McMahon et al Development 108; 281–287) and has been implicated in the regulation of growth and differentiation of osteoblastic cells (Chaudhary et al Mol. Cell. Biochem. 156; 69–77, 1996). Egr-1 and the closely related zinc finger transcription factor Wilm's Tumour 1 (WT1) have been implicated in the regulation of osteoclastogenesis (Kukita et al Endocrinology 138; 4384–4389, 1997) and both prostacyclin E2 (PGE2) and EGF are induced by Egr1 (Fang et al Calcified Tissue International 57; 450–455, 1995; Fang et al Prostoglandins, Leukotrienes and Essential Fatty Acids 54; 109–114, 1996). Vascular calcification is an actively regulated process similar to bone formation involving cells and factors known to be important in the regulation of bone metabolism (reviewed in Dermer et al Trends Cardiovasc. Med. 4; 45–49, 1994). Regulators of osteoblastogenesis and/or osteoclastogenesis may modulate the degree of vessel wall calcification.

Hypertrophic stimuli such as haemodynamic load and angiotensin II may be used to drive the production of egr-1 dominant negative under the control of a myocyte specific promoter and have application in the trreatment of heart failure.

Egr-1 is essential for Schwann cell expression of the p75 nerve growth factor (NGF) receptor (Nikam et al Mol. Cell. Neurosciences 6; 337–348, 1995). NGF induces Egr-1 expression with concomitant activation of growth factors (Kendall et al Brain Research. Molecular Brain Research. 25; 73–79, 1994; Kujubu et al Journal of Neuroscience Research 36; 58–65, 1993).

It has now been found that administration of a polynucleotide encoding transcription factor Egr-1 at a site of wounding, and subsequent expression thereof, promotes accelerated healing.

Thus, according to a first aspect of the present invention, there is provided the use of a nucleic acid molecule comprising a sequence encoding an Egr-1 transcription factor polypeptide or a biologically active fragment thereof in the manufacture of a medicament for the treatment of wounds in a mammal, including human.

For the avoidance of any doubt, reference to a polynucleotide is equivalent to any reference to a nucleic acid molecule.

According to a second aspect of the present invention, there is provided a method of treatment of wounds in a mammal, including human, which method comprises the administration to the mammal of a nucleic acid molecule comprising a sequence encoding an Egr-1 transcription factor polypeptide or a biologically active fragment thereof.

According to a third aspect, the invention provides a nucleic acid molecule comprising a sequence encoding an Egr-1 transcription factor polypeptide or a biologically active fragment thereof for use in the treatment of wounds.

In a fourth aspect, the invention provides a pharmaceutical composition comprising a nucleic acid molecule comprising a sequence encoding Egr-1 or a biologically active fragment thereof together with one or more pharmaceutically acceptable carriers thereof.

The present invention thus relates to the therapeutic use in the treatment of wounds of polynucleotides encoding an Egr-1 transcription factor. The invention also relates to therapeutic use in the treatment of wounds of an Egr-1 transcription factor itself, as described in greater detail below.

The invention relates to the use of Egr-1 polypeptides and nucleic acid sequences encoding Egr-1 from any origin or species. The protein sequences are highly conserved between species, for example with 98% homology between rat and mouse. The murine Egr-1 DNA sequence is known (*Cell*, 53 37–43 (1988)). The deduced amino acid sequence shows a long open reading frame with a stop codon (TM) at position 1858. The deduced amino acid sequence predicts a polypeptide of 533 amino acids with a molecular weight of 56, 596. The corresponding sequences from other species may be obtained by methods known in the art, for example by the screening of genomic or cDNA libraries using as probes oligonucleotide sequences based on or deriving from the murine Egr-1 sequence. Human Egr-1 is known to be located on chromosome 5, more precisely at 5 q23–31 (*Cell* 53, 37–43). The sequence of the human Egr-1 cDNA is described in Nucleic Acids Research 18 p42–83, 1990. The similarity between the mouse and human sequences is 87% and 94% at the nucleoside and protein levels, respectively.

References to Egr-1 polypeptides and polynucleotides described hereinafter are generally applicable to the sequences of any origin, including the murine Egr-1 DNA and corresponding amino acid sequences as published in *Cell*, 53 37–43 (1988) and the human sequence as published in *Nucleic Acids Research* 18 p4283, 1990 and to sequences from other species. As will be described below, the term Egr-1 also includes variants, fragments and analogues of Egr-1. Most preferably, the human sequence is used.

The following illustrative explanations are provided to facilitate understanding of certain terms used herein. The explanations are provided as a convenience and are not limitative of the invention.

"Treatment of wounds" includes treatment of conditions associated with wounds, wound healing and associated conditions and therapy which promotes, augments or accelerates healing of tissues and includes the treatment of limb ulcerations in diabetes and peripheral arterial occlusive disease, post-operative scarring, burns, psoriasis, acceleration of tissue remodelling and bone repair and the promotion of angiogenesis, re-endothelialisation following percutaneous trans-luminal coronary angioplasty, inhibition of left ventricular cardiac hypertrophy, modulation of vessel wall calcification, and promotion of neuroregeneration. It further includes inhibition of fibrotic conditions, for example, pulmonary and liver fibrosis, and prevention of alopecia.

A "biologically active fragment" of Egr-1 as referred to herein is a fragment which has Egr-1 activity, including wound healing properties according to the present invention.

"Genetic element" generally means a polynucleotide comprising a region that encodes a polypeptide, or a polynucleotide region that regulates replication, transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be comprised within plasmids. Genetic elements also may be comprised within a host cell genome; not in their natural state but, rather, following manipulation such as isolation, cloning and introduction into a host cell in the form of purified DNA or in a vector, among others.

A "host cell" is a cell which has been transformed or transfected, or is capable of transformation or transfection by an exogenous polynucleotide sequence.

"Identity", as known in the art, is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Identity can be readily calculated (*Computational Molecular Biology*, Lesk, A. M., ed., Oxford University Press, New York, 1988; Biocomputing: *Informatics and Genome Projects*, Smith, D. W., ed., Academic Press, New York, 1993; Computer Analysis of Sequence Data, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or two polypeptide sequences, the term is well known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., *SIAM J. Applied Math.*, 48: 1073 (1988). Methods commonly employed to determine identity between sequences include, but are not limited to those disclosed in Carillo, H., and Lipman, D., *SIAM J. Applied Math.*, 48:1073 (1988). Preferred methods to determine identity are designed to give the largest match between the sequences tested. Methods to determine identity are codified in computer programs. Preferred computer program methods to determine identity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol.* 215: 403 (1990)).

"Isolated" means altered "by the hand of man" from its natural state; i.e. that, if it occurs in nature, it has been changed or removed from its original environment, or both. For example, a naturally occurring polynucleotide or a polypeptide naturally present in a living organism in its natural state is not "isolated", but the same polynucleotide or polypeptide separated from the coexisting materials of its natural state is "isolated", as the term is employed herein. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotide sequences such as in the form of vectors, can be introduced into host cells, in culture or in whole organisms. Introduced into host cells in culture or in whole organisms, such DNAs still would be isolated, as the term is used herein, because they would not be in their naturally occurring form or environment which are not naturally occurring compositions, and, therein remain isolated polynucleotides or polypeptides within the meaning of that term as it is employed herein.

"Polynucleotide(s)" generally refers to any polyribonucleotide or polydeoxribonucleotide, which may be unmodified RNA or DNA or modified RNA or DNA or cDNA. Thus, for instance, polynucleotides as used herein refers to, among others, single-and double-stranded DNA, DNA that is a mixture of single-and double-stranded regions or single-, double-and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single-and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s).

"Polypeptide(s)", as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Among the known modifications which may be present in polypeptides for use in the present invention are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulphide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulphation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulphation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., Meth. Enzymol. 182:626–646 (1990) and Rattan et al., Protein Synthesis: Posttranslational Modifications and Aging, Ann. N.Y. Acad. Sci. 663: 48–62 (1992). It will be appreciated, as is well known and as noted above, that polypeptides are not always entirely linear. For instance, polypeptides may be generally as a result of post-translational events, including natural processing event and events brought about by human manipulation which do not occur naturally. Circular, branched and branched circular polypeptides may be synthesised by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionineless amino terminal variants of the protein of the invention. The modifications that occur in a polypeptide often will be a function of how it is made. For polypeptides made by expressing a cloned gene in a host, for instance, the nature and extent of the modifications in large part will be determined by the host cell post-translational modification capacity and the modification signals present in the polypeptide amino acid sequence. For instance, as is well known, glycosylation often does not occur in bacterial hosts such as, for example, E. coli. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having native patterns of glycosylation, inter alia. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesised recombinantly by expressing a polynucleotide in a host cell.

"Variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail. (1) A polynucleotide that differs in nucleotide sequence from another, reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type, a variant polynucleotide will encode a polypeptide with the same amino acid sequence as the reference. Also as noted below, changes in the nucleotide sequence of the variant polynucleotide may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. (2) A polypeptide that differs in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination.

"Treatment/Therapy" includes any regime that can benefit a human or non-human animal. The treatment may be in respect of an existing condition or may be prophylactic (preventative treatment).

"Comprising/Having" cover anything consisting of a specified feature/characteristic, as well as anything with that feature/characteristic, but which also has one or more additional features/characteristics. Thus in the case of a nucleic acid/protein sequence comprising/having a given sequence, the sequence itself is covered, as are longer sequences.

"Homologue" is used to cover any variant of a specified biologically active molecule that has one or more of the biological activities of that molecule.

The invention relates to therapeutic uses of nucleic acid molecules comprising a sequence which encodes an Egr-1 potypeptide. The invention relates also to therapeutic uses of fragments of said polynucleotide sequence which encode biologically active fragments of an Egr-1 or variants of the polynucleotide sequence which, by virtue of the degeneracy of the genetic code, encode functional, i.e. biologically active, fragments of Egr-1, and to functionally equivalent allelic variants and related sequences modified by single or multiple base substitution, addition and/or deletion which encode polypeptides having Egr-1 activity.

These may be obtained by standard cloning procedures known to the persons skilled in the art.

Polynucleotides encoding Egr-1 transcription factor may be in the form of DNA, cDNA or RNA, such as mRNA obtained by cloning or produced by chemical synthetic techniques. The DNA may be single or double stranded. Single stranded DNA may be the coding or sense strand, or it may be the non-coding or anti-sense strand. For therapeutic use, the polynucleotide is in a form capable of being expressed to a functional Egr-1 transcription factor at the wound site in the subject to be treated. The polynucleotides may also be used for in vitro production of Egr-1 polypeptide for administration in a further therapeutic aspect of the invention, as described in detail below.

Polynucleotides of the present invention which encode a polypeptide of Egr-1 transcription factor may include, but are not limited to, the coding sequence for Egr-1 polypeptide or biologically active fragments thereof. Thus, the polynucleotide may be provided together with additional, non-coding sequences, including, for example but not limited to, non-coding 5' and 3' sequences, such as the transcribed, non-translated sequences that play a role in transcription (including termination signals, for example), ribosome binding, mRNA stability elements, and additional coding sequence which encode additional amino acids, such as those which provide additional functionalities. Polynucleotides of the invention also include, but are not limited to, polynucleotides comprising a structural gene for Egr-1 and its naturally associated genetic elements.

In accordance with the foregoing, the term "polynucleotide encoding a polypeptide" as used herein encompasses polynucleotides which include a sequence encoding a polypeptide of Egr 1 transcription factor. The term encompasses polynucleotides that include a single continuous region or discontinuous regions encoding the polypeptide (for example, interrupted by integrated phage or insertion sequence or editing) together with additional regions, that also may contain coding and/or non-coding sequences.

The present invention further relates to variants of the herein above described polynucleotides which encode fragments, analogues and derivatives of the polypeptide. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Further preferred embodiments of the invention are polynucleotides that are at least 70% identical over their entire length to a polynucleotide encoding a polypeptide having the amino acid sequence set out in *Cell* 53 37–43 (1988) (the mouse sequence), more preferably at least 70% identical over the entire length to a polynucleotide encoding the human cDNA sequence and polynucleotides complementary thereto (the human sequence) in *Nucleic Acids Research* 18 4283, 1990 and polynucleotides which are complementary to such polynucleotides. Alternatively, most highly preferred are polynucleotides that comprise a region that is at least 80% identical over their entire length to a polynucleotide encoding a polypeptide of the present invention. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments in this respect, moreover, are polynucleotides which encode polypeptides which retain substantially the same biological function or activity as the mature Egr-1 polypeptide encoded by the murine DNA sequence in *Cell* 53 37–43 (1988), more preferably that encoded by the human sequence in *Nucleic Acids Research* 18 4283, 1990.

The present invention further relates to polynucleotides that hybridise to the herein above-described sequences. In this regard, the present invention especially relates to polynucleotides which hybridise under stringent conditions to the herein above-described polynucleotides. As herein used, the term "stringent conditions" means hybridisation will occur if there is at least 95% and preferably at least 97% identity between the sequences. Preferably, the sequences which hybridise in this manner to the sequence of the invention encode a polypeptide having the biological activity of Egr-1.

The polynucleotides may encode a polypeptide which is the mature protein plus additional amino or carboxylterminal amino acids. Such additional sequences may play a role for example, may lengthen or shorten protein half-life or may facilitate manipulation of a protein for assay or production, among other things. As generally is the case in vivo, the additional amino acids may be processed away from the mature protein by cellular enzymes.

Polynucleotides for use in the gene therapy aspect of the invention may be provided alone, or as part of a vector, such as an expression vector, examples of which are well known in the art.

An Egr-1 encoding polynucleotide may be used therapeutically in the method of the invention by way of gene therapy in which the polynucleotide is administered to a wound site or to other tissues in need of healing in a form in which it is capable of directing the production of Egr-1, or a biologically active fragment thereof, in situ. It is believed that Egr-1 acts to promote wound healing by activating genes involved in wound healing, such as genes for VEGF, PDGF, EGF, TGF beta, basic fibroblast growth factor, UPA and tissue factor.

Preferably in gene therapy, the polynucleotide is administered such that it is expressed in the subject to be treated for example in the form of a recombinant DNA molecule comprising a polynucleotide encoding Egr-1 operatively linked to a nucleic acid sequence which controls expression, such as in an expression vector. Such a vector will thus include appropriate transcriptional control signals including a promoter region capable of expressing the coding sequence, said promoter being operable in the subject to be treated. Thus for human gene therapy, the promoter, which term includes not only the sequence necessary to direct RNA polymerase to the transcriptional start site, but also, if appropriate, other operating or controlling sequences including enhancers, is preferably a human promoter sequence from a human gene, or from a gene which is typically expressed in humans, such as the promoter from human cytomegalovirus (CMV). Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-1 promoter.

As discussed in more detail below, the native Egr-1 promoter may be used. The present inventors have found that the published sequence provided for the human Egr-1 promoter is not correct and have provided a novel sequence with various differences from said published sequence.

A polynucleotide sequence and transcriptional control sequence may be provided cloned into a replicable plasmid vector, based on commercially available plasmids, such as pBR322, or may be constructed from available plasmids by routine application of well known, published procedures.

The vector may also include transcriptional control signals, situated 3' to the Egr-1 encoding sequence, and also polyadenylation signals, recognisable in the subject to be treated, such as, for example, the corresponding sequences from viruses such as, for human treatment, the SV40 virus. Other transcriptional controlling sequences are well known in the art and may be used.

The expression vectors may also include selectable markers, such as for antibiotic resistance, which enable the vectors to be propagated.

Expression vectors capable in situ of synthesising Egr-1 may be introduced into the wound site directly by physical methods. Examples of these include topical application of the 'naked' nucleic acid vector in an appropriate vehicle for example in solution in a pharmaceutically acceptable excipient such as phosphate buffered saline (PBS), or administration of the vector by physical methods such as particle bombardment, also known as 'gene gun' technology, according to methods known in the art e.g. as described in U.S. Pat. No. 5,371,015 in which inert particles, such as gold beads coated with the vector are accelerated at speeds sufficient to enable them to penetrate the surface at the wound site e.g. skin cells, by means of discharge under high pressure from a projecting device. (Particles coated with a nucleic acid molecule of the present invention are within the scope of the present invention, as are devices comprising such particles.)

Other physical methods of administering the DNA directly to the recipient include ultrasound, electrical stimulation, electroporation and microseeding.

Particularly preferred is the microseeding mode of delivery which is a system for delivering genetic material into cells in situ in a patient. This method is described in U.S. Pat. No. 5,697,901.

Egr-1 encoding nucleic acid sequence for use in the therapy of the invention may also be administered by means of delivery vectors. These include viral delivery vectors, such as adenovirus or retrovirus delivery vectors known in the art.

Other non-viral delivery vectors include lipid delivery vectors, including liposome delivery vehicles, known in the art.

An Egr-1 encoding nucleic acid sequence may also be administered to the wound site by means of transformed host cells. Such cells include cells harvested from the subject, into which the nucleic acid sequence is introduced by gene transfer methods known in the art, followed by growth of the transformed cells in culture and grafting to the subject.

Expression constructs such as those described above may be used in a variety of ways in the therapy of the present invention. Thus, they may be directly administered to the wound site in the subject, or they may be used to prepare recombinant Egr-1 transcription factor itself which can then be administered to the wound site as is discussed in more detail below. The invention also relates to host cells which are genetically engineered with constructs which comprise Egr-1 polynucleotide or polynucleotides of the present invention or genetic elements defined hereinabove, and to the uses of these vectors and cells in the therapeutic methods of the invention. These constructs may be used per se in the therapeutic methods of the invention or they may be used to prepare an Egr-1 polypeptide for use in the therapeutic methods of the invention described in greater detail below.

The vector may be, for example, a plasmid vector, a single or double-stranded phage vector, a single or double-stranded RNA or DNA viral vector, depending upon whether the vector is to be administered directly at the wound site (i.e. for in situ synthesis of Egr-1), or is to be used for synthesis of recombinant Egr-1. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art.

Generally, vectors for expressing an Egr-1 polypeptide for use in the invention comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain embodiments in this regard, the vectors provide for specific expression. For production of recombinant Egr-1, such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

A great variety of expression vectors can be used to express Egr-1 for use in the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques, such as, for example, those set forth in Sambrook et al., MOLECULAR CLONING, A LABORATORY MANUAL, 2nd Ed.; Cold Spring Harbor Laboratory Press, Cold Spring Harbar, N.Y. (1989).

The nucleic acid sequence in the expression vector is operatively linked to appropriate expression control sequence(s), including, for instance, a promoter to direct mRNA transcription. Representatives of such promoters include, but are not limited to, the phage lambda PL promoter, the *E. coli* lac, trp and tac promoters, for recombinant expression, and the SV40 early and late promoters and promoters of retroviral LTRs for in situ expression.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly-practised procedures, such regions will operate by controlling transcription, such as transcription factors, repressor binding sites and termination, among others.

Vectors for propagation and expression generally will include selectable markers and amplification regions, such as, for example, those set forth in Sambrook et al., MOLECULAR CLONING, A LABORATORY MANUAL, 2nd Ed.; Cold Spring Harbor Laboratory Press, Cold Spring Harbar, N.Y. (1989).

Representative examples of appropriate hosts for recombinant expression of Egr-1 include bacterial cells, such as streptococci, staphylococci, *E. coli*, streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia, and pBR322 (ATCC 37017). Among preferred eukaryotic vectors are pWLNEO, pSV2CAT, pOG44, pXT1 and pSG available from Stratagene; and pSVK3, pBPV, pMSG and pSVL available from Pharmacia. These vectors which can be used both for recombinant expression and for in situ expression are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide for use in the therapy of the invention in a host may be used in this aspect of the invention.

Examples of vectors for use in this aspect of the invention include expression vectors in which the Egr-1 cDNA sequence is inserted in a plasmid whereby gene expression is driven from the human immediate early cytomegalovirus enhancer-promoter (Foecking and Hofstetter, *Cell*, 45, 101–105, 1986). Such expression plasmids may contain SV40 RNA processing signals such as polyadenylation and termination signals. Expression constructs which use the CMV promoter and that are commercially available are pCDM8, pcDNA1 and derivatives, pcDNA3 and derivatives (Invitrogen). Other expression vectors available which may be used are pSVK3 and pSVL which contain the SV40 promoter and mRNA splice site and polyadenylation signals from SV40 (pSVK3) and SV40 VP1 processing signals (PSVL; vectors from Pharmacia).

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available, such as pKK232-8 and pCM7. Promoters for expression of polynucleotides for use in the therapy of the present invention include not only well known and readily available promoters, but also promoters that readily may be obtained by the foregoing technique, using a reporter gene; for in situ expression, such a promoter should desirably be recognised in the subject to be treated.

Among known prokaryotic promoters suitable for expression of polynucleotides and polypeptides in accordance with the therapy of the present invention are the *E. coli* lad and lacZ and promoters, the T3 and T7 promoters, the gpt promoter, the lambda PR, PL promoters and the trp promoter.

Recombinant expression vectors will include, for example, origins of replication, a promoter preferably derived from a highly-expressed gene to direct transcription of a downstream structural sequence, and a selectable marker to permit isolation of vector containing cells after exposure to the vector.

Polynucleotides for use in the therapy of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed.

Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signal appropriately disposed at the 3' end of the transcribed region may also be included in the polynucleotide construct.

For secretion of the translated protein into the lumen of the endoplasmic reticulum, into the periplasmic space or into the extracellular environment, appropriate secretion signals may be incorporated into the expressed polypeptide when recombinantly synthesised. These signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N- or C-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability or to facilitate purification, among others, are familiar and routine techniques in the art. A preferred fusion protein comprises a heterologous region from immunolglobulin that is useful to solubilize or purify polypeptides. Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Mammalian expression vectors may comprise an origin of replication, a suitable promoter and enhancer, and also any necessary ribosome binding sites, polyadenylation regions, splice donor and acceptor sites, transcriptional termination sequences, and 5' flanking non-transcribed sequences that are necessary for expression.

For preparing Egr-1 polypeptides for use in the invention genetically engineered host cells may be used. Introduction of a polynucleotides into the host cell can be affected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis et al., BASIC METHODS IN MOLECULAR BIOLOGY, (1986) and Sambrook etal., MOLECULAR CLONING: A LABORATORY MANUAL, 2nd Ed., Cold Spring Harbor Laboratory Press, Cold Spring Harbor, N.Y. (1989).

Mature proteins can be expressed in host cells including mammalian cells such as CHO cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

The polypeptide can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding protein may be employed to regenerate active conformation when the polypeptide is denatured during isolation and or purification.

For therapy, an Egr-1 encoding polynucleotide e.g. in the form of a recombinant vector, may be purified by techniques known in the art, such as by means of column chromatography as described in Sambrook et al., MOLECULAR CLONING: A LABORATORY MANUAL, 2nd Ed., Cold Spring Harbor Laboratory Press, Cold Spring Harbor, N.Y. (1989).

As indicated above, Egr-1 may be administered at the site of wounding either as an Egr-1 encoding nucleic acid which is transcribed and translated to Egr-1 at the wound site itself in a form of gene therapy, or the transcription factor itself may be directly administered.

Thus, according to a fifth aspect of the invention, there is provided the use of an Egr-1 transcription factor polypeptide or a biologically active fragment thereof in the manufacture of a medicament for the treatment of wounds in a mammal, including human.

According to a sixth aspect of the invention, there is provided a method of treatment of wounds in a mammal, including human, which comprises the administration to the mammal of a therapeutically effective amount of an Egr-1 transcription factor polypeptide or a biologically active fragment thereof.

In a seventh aspect, the invention provides the use of an Egr-1 transcription factor or a biologically active fragment thereof for use the treatment of wounds and in wound healing.

In an eighth aspect, the invention provides a pharmaceutical composition comprising Egr-1 transcription factor or a biologically active fragment thereof together with one or more pharmaceutically acceptable carriers thereof.

As used herein, the term "Egr-1 transcription factor polypeptide" includes naturally and recombinantly produced Egr-1 transcription factor, natural, synthetic and biologically active polypeptide analogues or variants or derivatives thereof or biologically active fragments thereof and variants, derivatives and analogues of said fragments.

Egr-1 transcription factor protein products including biologically active fragments of Egr-1 transcription factor may be generated and/or isolated by general techniques known in the art.

Egr-1 and the aforementioned fragments and derivatives thereof for use in the therapy of the invention may be extracted from natural sources by methods known in the art. Such methods include purification by means of sequence specific DNA affinity chromatography using methods such as those described in Briggs et al, Science 234, 47–52, 1986, using a DNA binding oligonucleotide which recognises Egr-1. The polypeptide may also be prepared by methods of recombinant DNA technology known to the art as described above, i.e. by expression in host cells of the constructs described. Alternatively, the polypeptides of the invention can be synthetically produced by conventional peptide synthesisers.

The invention also relates to uses of fragments, analogues and derivatives of Egr-1. The terms "fragment", "derivative" and "analogue" means a polypeptide which retains essentially the same biological function or activity as such polypeptide. Thus, an analogue includes a proprotein which can be activated by cleavage of the proprotein portion to produce an active mature polypeptide.

The fragment, derivative or analogue of the polypeptide may be (i) one in which one or more of the amino acid residues are substituted with a conserved or non-conserved amino acid residue (preferably, a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogues are deemed to be within the scope of those skilled in the art from the teachings herein.

Among preferred variants are those that vary from naturally occurring Egr-1 by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and lie; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogues, derivatives and fragments, and variants, analogues and derivatives of the fragments, having the amino acid sequence of the polypeptide in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the polypeptide of the present invention. Also especially preferred in this regard are conservative substitutions.

Particularly preferred fragments are biologically active fragments i.e. fragments which retain the wound healing properties of the parent polypeptide.

The polypeptides and polynucleotides useful in the present invention are preferably provided in an isolated form, and preferably are purified to homogeneity.

Egr-1 polypeptides for use in the present invention include Egr-1 polypeptide as well as polypeptides which have at least 70% identity preferably at least 80% identity to and more preferably at least 90% more identity and still more preferably at least 95% similarity (still more preferably at least 99% identity) to the murine polypeptide sequence as set out in *Cell* 53 37–43 (1988) and to polypeptides encoded by the human sequence and also include portions of such polypeptides with such portion of the polypeptide generally containing at least 30 amino acids and more preferably at least 50 amino acids.

Fragments or portions of the polypeptides useful in the therapy of the present invention may be employed for producing the corresponding full-length polypeptide by peptide synthesis; therefore, the fragments may be employed as intermediates for producing the full-length polypeptides. Fragments or portions of the polynucleotides useful in the present invention may be used to synthesise full-length polynucleotides useful in the present invention.

The invention also relates to the use of fragments of an Egr-1 polypeptide defined hereinabove and fragments of variants and derivatives thereof.

In this regard, a fragment is a polypeptide having an amino acid sequence that entirely is the same as part but not all of the amino acid sequence of Egr-1 polypeptides and variants or derivatives thereof.

Such fragments may be "free-standing", i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a polypeptide of the present invention comprised within a precursor potypeptide designed for expression in a host and having heterologous pre- and propolypeptide regions fused to the amino terminus of the fragment and an additional region fused to the carboxyl terminus of the fragment. Therefore, fragments in one aspect of the meaning intended herein, refers to the portion or portions of a fusion polypeptide or fusion protein derived from a polypeptide of the present invention.

Also preferred in this aspect of the invention are fragments characterised by structural or functional attributes of the polypeptide useful in the therapy of the present invention. Preferred embodiments of the invention in this regard include fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions of the polypeptide of the present invention, and combinations of such fragments.

Preferred regions are those that mediate activities of the polypeptide of the present invention. Most highly preferred in this regard are fragments that have a chemical, biological or other activity of the polypeptide of the present invention, including those with a similar activity or an improved activity, or with a decreased undesirable activity. Further preferred polypeptide fragments are those that comprise or contain antigenic or immunogenic determinants in an animal, especially in a human.

It will be appreciated that the invention also relates to, among others, polynucleotides encoding the aforementioned fragments, polynucleotides that hybridise to polynucleotides encoding the fragments, particularly those that hybridise under stringent conditions, and polynucleotides, such as PCR primers, for amplifying polynucleotides that encode the fragments. In these regards, preferred polynucleotides are those that correspond to the preferred fragments, as discussed above Further embodiments of this aspect of the invention include biologically, prophylactically, clinically or therapeutically useful variants, analogues or derivatives thereof, or fragments thereof, including fragments of the variants, analogues and derivatives and compositions comprising the same. Biologically active variants, analogues or fragments are included in the scope of the present invention.

The invention also relates to compositions comprising the polynucleotides or polypeptides discussed above. Therefore, polynucleotides or polypeptides of the present invention may be employed in combination with a pharmaceutically acceptable carrier or carriers.

Such carriers may include, but are not limited to saline, buffered saline, dextrose, water, glycerol, ethanol and combinations thereof.

Polypeptides and polynucleotides may be employed in the present invention may alone or in conjunction with other compounds, such as therapeutic compounds.

The pharmaceutical compositions may be administered in any effective, convenient manner effective for targeting wound sites including, for instance, administration by topical, intravenous, intramuscular, intranasal or intradermal routes among others. Generally, the compositions will be locally applied to the wound or associated condition.

In therapy or as a prophylactic, the active agent may be administered to an individual as an injectable composition, for example as a sterile aqueous dispersion, preferably isotonic.

Alternatively, the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

As a ninth aspect, there is provided a pharmaceutical composition comprising Egr-1 transcription factor or a nucleic acid molecule comprising a sequence encoding Egr-1 together with one or more pharmaceutically acceptable carriers thereof.

The therapeutic advantage of using transcription factors in accelerated wound healing is in the activation of multiple target genes which promote accelerated healing. Egr-1 is naturally activated in response to wounding and augmenting the natural response is also an advantage. The treatment is DNA based and it provides a reliable and reproducible delivery system.

Where an Egr-1 polynucleotide is used in the therapeutic method of the invention, the polynucleotide may be used as part of an expression construct e.g. in the form of an expression vector. In such a method, the construct is introduced at the wound site where Egr-1 is produced in situ. The constructs used may be standard vectors and/or gene delivery systems, such as liposomes, receptor-mediated delivery systems and viral vectors.

The present invention is suitable for all aspects of wound healing including limb ulcerations in diabetes and peripheral arterial occlusive disease, post-operative scarring, burns and psoriasis.

As described above, Egr-1 polypeptides or nucleic acids of the present invention may be administered locally to the site of tissue damage by any convenient method e.g. by topical administration. One method of delivery of nucleic acid products is using gene gun technology in which the Egr-1 isolated nucleic acid molecule e.g. in the form of cDNA or in an expression vector is immobilised on gold particles and fired directly at the site of wounding. Thus, as a preferred aspect of the present invention, there is provided the use of a nucleic acid molecule comprising a sequence encoding Egr-1 in a gene gun for the treatment of wounds. Further, there is provided a composition suitable for gene gun therapy comprising an Egr-1 transcription factor encoding sequence and gold particles.

Preferred delivery of the nucleic acid or polypeptide of the invention however is by microseeding as described in U.S. Pat. No. 5,697,901.

As mentioned previously, the polynucleotide comprising a sequence encoding Egr-1 or a biologically-active fragment thereof may be under the control of at least a part of a native Egr-1 promoter, preferably the human Egr-1 promoter.

The murine Egr-1 promoter has been isolated and sequenced (Morris, *Nucleic Acid Research*, 16: 8835–3346). Potential regulatory sequences include an AAATA element (a 'TATA' like homology) at position −26 to −22; a CCAAT box at positions −337 to −333; five serum response elements (SREs) at positions −110 to −91, −342 to −324, −358 to −339, −374 to −355 and −412 to −393; two Ap1 sites at positions −610 to −603 and −867 to −860; four Sp1 sites at positions −285 to −280, −649 to −644, −700 to −695 and −719 to −714; and two cAMP response elements at positions −138 to −131 and −631 to −624. Egr-1 has been shown to bind to the murine Egr-1 promoter and to down-regulate the transcription of its own expression. The sequence of this promoter is provided in FIG. 9 of the accompanying drawings.

Less is understood about the regulation of the human Egr-1 promoter. A purported human Egr-1 sequence has been provided. 695 nucleotides of upstream sequence have been identified relative to the mRNA start site at +1. This upstream sequence comprises an AAATA element (a 'TATA' like homology) at position −26 to −22, and numerous potential regulatory elements including two Sp1 sites at positions −505 to −499, and −647 to −642; two cyclic AMP response elements at positions −134 to −127 and −630 to −623, five serum-response elements (SREs) at positions −108 to −89, −344 to −326, −359 to −340, −376 to −357 and −410 to −394; an Egr-1 binding site (EBS) at position −597 to −589 and a tetra-decanoyl phorbol acetate (TPA) responsive element (Ap1 binding site) at position −609 to −602. It is known that the TPA binding site is functional as TPA stimulates expression from a plasmid expressing the chloramphenicol acetyl transferase gene. SREs 3 and 4 have been shown to mediate the response of the Egr-1 promoter to shear stress and can confer shear stress response on the SV40 promoter. Deletion of the EBS from the human promoter element leads to an increase in the shear stress responsiveness of this promoter, arguing for a role of Egr-1 in down-regulating activity from the human promoter.

The present inventors have found that the published sequence provided for the human Egr-1 promoter is not correct and have provided a novel sequence with various differences from said published sequence. These sequence differences could not have been predicted in advance and at least some of them are considered to be functionally significant. Furthermore, the present inventors have provided a complete sequence, whereas the reported human Egr-1 promoter sequence includes various gaps.

Thus, the nucleic acid molecule comprising a sequence encoding Egr-1 or a biologically-active fragment thereof may be operatively linked to a nucleic acid sequence which:

a) has a strand comprising the sequence provided in FIG. 7 for GW SEQ; or b) has a strand comprising one or more deletions, insertions and/or substitutions relative to GW SEQ, but which does not comprise the sequence shown in FIG. 7 as ON SEQ and which also does not comprise the sequence shown in FIG. 9.

According to a tenth aspect of the present invention, there is provided a nucleic acid molecule which:

a) has a strand comprising the sequence provided in FIG. 7 for GW SEQ;

b) has a strand comprising one or more deletions, insertions and/or substitutions relative to GW SEQ, but which does not comprise the sequence shown in FIG. 7 as ON SEQ and which also does not comprise the sequence shown in FIG. 9; or c) has a strand that hybridises with a strand as described in a) or b) above.

Molecules within the scope of a), b) or c) above will now be described in greater detail:

a) A Nucleic Acid Molecule Having the Sequence Provided in FIG. 7 for GW SEQ It can be seen that the GW SEQ shown in FIG. 7 has various boxed regions. These are believed to be functionally significant. Without being bound by theory, purported functions of the various boxed regions shown in FIG. 7 are described below:

Sp1 (Two Regions)

Sp1 denotes a sequence for binding transcription factor Sp1 and homologues.

cAMP RE (Two Regions)

cAMP RE denotes a sequence for the binding of transcription factor ATF and homologues. This is induced by cAMP and the sequence is therefore referred to as a cAMP response element.

TPA RE

TPA RE denotes a sequence for binding of the transcription factor AP1 and homologues. This is induced, for example, by the phorbol ester TPA and the sequence is therefore referred to as a TPA response element.

EBS

EBS denotes a sequence for the binding of transcription factor Egr-1 and homologues.

SRE (SRE5, SRE4, SRE3, SRE2, SRE1)

SRE denotes a sequence providing serum responsiveness (i.e. a serum response element). Together with associated Ets (E26-transformation specific) binding sites serum response elements bind transcription factors such as SRF, Elk-1 and/or F-ACT1, as well as homologues thereof.

TATA

The TATA box is believed to be required for the assembly of the transcription complex, which comprises many transcription factors required for transcription initiation. It need not include the exact sequence "TATA" since this is a consensus sequence, and a certain degree of variation can occur.

GW SEQ has various sequence differences relative to the published human Egr-1 sequence (designated herein as "ON SEQ"). The differences will now be discussed in respect of an alignment of the sequences GW SEQ and ON SEQ shown in FIG. 7.

As can be seen from FIG. 7, GW SEQ has five nucleotides that are changed from the specific nucleotides provided at the corresponding positions for ON SEQ. These can be considered as substitutions relative to the ON SEQ. Two of these are present in regions that are boxed. These two substitutions are the substitution of a G with a T and the substitution of a G with a C. They are present in the first cAMP RE box and in the SRE3 box respectively.

GW SEQ also has various additional nucleotides relative to ON SEQ (i.e. nucleotides that are not specifically identified in ON SEQ). These can be regarded as insertions relative to ON SEQ. Four of these are present in the SRE5 box. (Three of these are insertions of an A and one is an insertion of a C.)

GW SEQ has one deletion relative to ON SEQ. It is the deletion of a G. This is not in a boxed region. It is located between the second Sp1 box and the SRE5 box.

Molecules within the scope of a) above may of course have additional upstream and/or downstream sequences relative to GW SEQ. For example, one or more regions involved in transcription/translation or the regulation thereof may be provided. A coding region may also be provided (preferably coding for Egr-1 or a biologically-active fragment thereof. Additional regions are discussed in greater detail later on.

b) A Nucleic Acid Molecule Which has a Strand Comprising one or More Deletions, Insertions and/or Substitutions Relative to GW SEQ, but Which Does not Comprise the Sequence Shown in FIG. 7 as ON SEQ and Which Also Does not Comprise the Sequence Shown in FIG. 9

Changes in nucleotide sequence can be made can be made relative to a molecule comprising GW SEQ to provide other molecules that are still of utility.

Such changes are within the scope of the present invention. They include allelic and non-allelic variants.

Preferred variants within the scope of b) above will usually comprise one or more regulatory regions having a function corresponding to the function of one or more of the boxed regions shown for GW SEQ (even if that function is up- or down-regulated relative to the one or more boxed regions shown for the GW SEQ). Most preferably, such molecules will have one or more regions having the same sequences as one or more of the boxed regions shown for GW SEQ.

Desirably variants within the scope of b) above will have substantial sequence identity with all or part said GW SEQ over the length of said GW SEQ or part thereof.

If a variant has one or more regions corresponding to one or more of the boxed regions shown in FIG. 7 for GW SEQ, it is preferred that there are no differences relative to said boxed regions or only a few such differences (e.g. it may generally be preferred to have a maximum of only 1,2 or 3 differences in respect of a given boxed region). There may be more sequence changes outside the boxed regions. Thus, variants may have relatively low degrees of sequence identity with the corresponding part of the GW SEQ in respect of regions that are not boxed in FIG. 7. Indeed, some variants may not have one or more regions corresponding to the one or more regions outside said boxed regions in respect of the GW SEQ.

Preferred nucleic acid molecules of the tenth aspect of the present invention will include one or more regulatory regions capable of altering the level of transcription of Egr-1 in mammals (most preferably in humans) in response to in vivo conditions. Thus, such nucleic acid molecules may be administered to mammals to provide Egr-1 in a manner allowing its expression to be regulated at the level of transcription (these nucleic acid molecules will therefore generally include a region encoding a substance having Egr-1 activity).

One or more serum response elements (SREs) may be present. Desirably one or more of these will be shear stress response elements (SSREs). These are regions that confer shear stress responsiveness on transcription.

A plurality of SSREs may co-operate in facilitating shear stress responsiveness. Desirably these are associated with/ include one or more Ets sites. However, in some cases, it is possible that only one SSRE need be present (preferably together with an Ets site) in order to provide a degree of shear stress responsiveness.

A preferred SSRE is indicated in FIG. 7 as SRE5 for "GW SEQ". The present inventors have shown that this is functional, whereas the SRE5 sequence shown in respect of ON SEQ is non-functional. SRE5 itself, as well as variants of SRE5 capable of providing shear stress responsiveness are within the scope of the present invention. Such variants preferably include at least one of the nucleotide differences present in the GW SEQ SRE5 relative to the ON SEQ SRE5.

Other preferred SSREs are SRE3 and SRE4 as shown in FIG. 7 for GW SEQ, as well as variants thereof capable of providing shear stress responsiveness.

Most preferably, all three of SRE3, SRE4 and SRE5 (or variants thereof capable of providing shear stress responsiveness) are present.

Irrespective of whether or not particular SREs are present, a nucleic acid molecule of the tenth aspect of the present invention will desirably include a TATA box (which will not necessarily include the consensus sequence "TATA"). It will usually also include a CCAAT box (which will not necessarily include the consensus sequence "CCMT").

At least one, and preferably two, Sp1 binding regions will usually also be present. The Sp1 binding regions may be either or both of the Sp1 binding sequences shown in FIG. 7 for GW SEQ.

A cAMP response region may be present. Preferred such regions comprise the sequences shown in FIG. 7 having the designation cAMP RE in respect of the GW SEQ. Most preferred is the first cAMP RE shown in FIG. 7 for GW SEQ. These can allow regulation of transcription by cAMP.

An Egr-1 binding site (EBS) may be present. This is believed to have an important role in down-regulating transcription of Egr-1 once levels of Egr-1 exceed a certain threshold. Thus, Egr-1 can limit its own expression following shear stress stimulation. An EBS will generally be included if it is desired to limit Egr-1 levels in this manner. The EBS may have the sequence shown in FIG. 7 for GW SEQ as EBS. Nucleotide changes can be made to a given EBS to provide variants thereof. For example, variants can be provided with reduced affinity for Egr-1 relative to the EBS shown in FIG. 7 for GW SEQ. One such variant is the EBS shown in FIG. 8. In some cases, a functional EBS may not be present and therefore regulation by Egr-1 can be abolished completely (e.g. a complete deletion of an EBS may be made). Nucleotide changes may also be made to an EBS to provide increased affinity for Egr-1. This is useful if it is desired to have increased self-regulation of Egr-1 expression.

c) A Nucleic Acid Molecule Which has a Strand That Hybridises With a Strand as Described in a) or b) Above Nucleic acid molecules that can hybridise to one or more of the nucleic acid molecules discussed above are also covered by the tenth aspect of the present invention. Such nucleic acid molecules are referred to herein as "hybridising" nucleic acid molecules. Desirably, hybridising molecules of the present invention are at least 10 nucleotides in length and preferably are at least 25, at least 50, at least 100, or at least 200 nucleotides in length.

A hybridising nucleic acid molecule of the present invention may have a high degree of sequence identity along its length with a nucleic acid molecule complementary to a nucleic acid within the scope of a) or b) above (e.g. at least 50%, at least 75%, at least 90%, at least 95% or at least 98% identity), although this is not essential. The greater the degree of sequence identity that a given single stranded nucleic acid molecule has with another single stranded nucleic acid molecule, the greater the likelihood that it will hybridise to a single stranded nucleic acid molecule that is complementary to that other single stranded nucleic acid molecule under appropriate conditions.

Preferred hybridising molecules hybridise under conditions of moderate or high stringency. Hybridisation conditions are discussed in detail at pp 1.101–1.110 and 11.45–11.61 of Sambrook et al (Molecular Cloning, 2nd Edition, Cold Spring Harbor Laboratory Press (1989)). One example of hybridisation conditions that can be used involves using a pre-washing solution of 5×SSC, 0.5% SDS, 1.0 mM EDTA (pH 8.0) and attempting hybridisation overnight at 55° C. using 5×SSC. However, there are many other possibilities. Some of these are listed in Table 1 of WO98/45435, for example (see especially the conditions set out under A–F of that table and, less preferably those listed under G to L or M to R).

Another approach is to determine the Tm for a given perfect duplex (i.e. with no mismatches) of a certain length under given conditions and then to perform attempted hybridisation with a single strand of the duplex under those conditions, but at a temperature sufficiently below the Tm to allow for formation of a range of stable hybrids at an acceptable rate, whilst still requiring a reasonable degree of hybridisation specificity. The Tm for such a duplex can be determined empirically by providing the duplex and gradually increasing the temperature until the Tm is achieved. The Tm can also be estimated e.g. by using: Tm=81.5+16.6 ($\log_{10}$[Na$^+$])+0.41 (fraction G+C–(600/N), where N is the chain length (this formula is reasonably accurate for Na$^+$ concentrations of 1M or less and for polynucleotide lengths of 14 to 70, but is less accurate when these parameters are not satisfied). For nucleic acid molecules of greater than 200 nucleotides in length, hybridisation may, for example, be carried out at 15 to 25° C. below the Tm of a perfect hybrid (i.e. with no mismatches) under given conditions. However, as the length is decreased, the Tm is lowered so that it is sometimes inconvenient to carry out hybridisation at Tm −25° C. Hybridisation with shorter nucleic acid molecules is therefore often carried out at only 5 to 10° C. below the Tm. Moderate or high stringency conditions will usually only allow a small proportion of mismatches. As a rule of thumb, for every 1% of mismatches, there is a reduction of Tm by 1–1.5° C. Preferably, hybridisation conditions are chosen to allow less than 25% mismatches, more preferably to allow less than 10% or less than 5% mismatches. Hybridisation can be followed by washes of increasing stringency. Thus, initial washes may be under conditions of low stringency, but these can be followed with higher stringency washes, up to the stringency of the conditions under which hybridisation was performed.

The foregoing discussion of hybridisation conditions is provided for general guidance but is not intended to be limiting. This is because a skilled person will be able to vary parameters as appropriate in order to provide suitable hybridisation conditions, and can take into account such variables as polynucleotide length, base composition, nature of duplex (i.e. DNA/DNA, RNA/RNA or DNA/RNA), type of ion present, etc.

Most preferably, hybridising nucleic acid molecules of the tenth aspect of the present invention hybridise to a DNA molecule having the sequence shown in FIG. 7 for GW SEQ or to one or more of the boxed regions shown in FIG. 7.

Hybridising nucleic acid molecules can be useful as probes or primers, for example.

Probes can be used to purify and/or to identify nucleic acids. They may be used in diagnosis. For example, probes may be used to determine whether or not an individual has defects in its genome that may affect the transcription of Egr-1 or the regulation of such transcription. Such defects may make the individual prone to various disorders that may be treatable using treatments of the present invention. For example, wound healing may be impaired by mutations in one or more of the SREs. Such mutations may be identified by using probes that hybridise with a greater degree of specificity to one or more of the SREs shown for GW SEQ than to the corresponding mutant SREs (or vice versa).

Desirably, hybridising molecules of the tenth aspect of the present invention hybridise more stringently to a DNA molecule having the sequence shown in FIG. 7 for GW SEQ or to one or more of the boxed regions thereof than to a DNA molecule having the sequence shown in FIG. 7 for ON SEQ or to one or more of the boxed regions thereof. For example, hybridising molecules can be designed with a high degree of specificity for one or more of the SRE3, SRE5 and cAMP regions shown for GW SEQ in FIG. 7 (all of these regions have differences in sequence from the corresponding regions of ON SEQ).

Hybridising nucleic acid molecules within the scope of the tenth aspect of the present invention include primers. Primers are useful in amplifying nucleic acids or parts thereof, e.g. by PCR techniques.

In addition to being useful as probes or primers, hybridising nucleic acid molecules of the tenth aspect of the present invention can be used as antisense molecules to alter expression. This technique can be used in antisense therapy. Antisense molecules can be used for example to block or reduce the expression of Egr-1 by preventing or reducing the level of transcription. Alternatively, they may be used to prevent or reduce the regulation of transcription of Egr-1 by a given regulator by binding to a region to which the regulator would normally bind.

It is important to note that nucleic acid molecules for use in the present invention include not only those with classical DNA or RNA structures, but also variants with modified (non-phosphodiester) backbones e.g. morpholino derivatives and peptide nucleic acids (PNAs), which contain an N-(2-aminoethyl)glycine-based pseudopeptide backbone (see Nielsen, P. E., *Annual Review of Biophysics & Biomolecular Structure*, 24 167–83 (1995)). Nucleic acid variants with modified backbones can have increased stability relative to unmodified nucleic acids and are particularly useful where long-term hybridisation is desired (e.g. in antisense therapy).

From the foregoing discussion, it will be appreciated that a large number of nucleic acids are within the scope of the tenth aspect of the present invention. Unless the context indicates otherwise, nucleic acid molecules of the tenth aspect of the present invention may therefore have one or more of the following characteristics:

1) They may be in the form of DNA or RNA (including variants of naturally occurring DNA or RNA structures, which have non-naturally occurring bases and/or non-naturally occurring backbones).
2) They may be single-stranded or double-stranded (both a given strand and its complement are included, whether or not they are associated).
3) They may be provided in recombinant form i.e. covalently linked to a heterologous 5' and/or 3' flanking sequence to provide a chimaeric molecule (e.g. a vector) which does not occur in nature.
4) They may be provided without 5' and/or 3' flanking sequences that normally occur in nature.
5) They may be provided in substantially pure form (e.g. in isolated form). This can be done for example by using probes to isolate cloned molecules having a desired target sequence or by using chemical synthesis techniques. Thus, the nucleic acids may be provided in a form which is substantially free from contaminating proteins and/or from other nucleic acids.

6) They may be provided with introns (e.g. as a full-length gene) or without introns Various uses of the tenth aspect of the present invention will now be discussed in further detail.

Nucleic acid molecules of the tenth aspect of the present invention may comprise any desired coding sequence. For example, one or more serum response elements may be operatively linked with a coding sequence that is normally not associated with such elements. This can be useful for example in wound healing if it is desired to provide serum responsiveness in respect of a given therapeutic agent encoded by the coding sequence that does not normally demonstrate serum responsiveness.

It is however preferred that nucleic acid molecules of the tenth aspect of the present invention comprise a coding sequence for Egr-1 or a biologically active fragment thereof.

Desirably, nucleic acid molecules of the tenth aspect of the present invention include a promoter region and can be used to provide Egr-1 by allowing for the transcription of Egr-1 mRNA. This can then be translated by ribosomes present in a host. Thus, nucleic acid molecules may be administered to a subject (preferably a human or other mammal) so that additional Egr-1 can be synthesised in the subject, or (less preferably) they may be used to prepare Egr-1 itself, which may then be administered to the subject.

Preferred nucleic acid molecules of the tenth aspect of the present invention for administration to a subject can be transcribed in such a manner so that transcription can be regulated by one or more factors that regulate Egr-1 transcription in the subject.

For example, one or more SSREs may be provided (as discussed above) to provide the transcription of Egr-1 with shear stress responsiveness. This is particularly advantageous where nucleic acid molecules of the tenth aspect of the present invention are administered to a patient (rather than administering Egr-1 itself). Shear stress responsiveness is beneficial where nucleic acid molecules of the tenth aspect of the present invention are used in vivo in treating wounds. This is because shear stress at wound sites can result in factors binding to SSREs that can stimulate increased transcription of Egr-1. The resultant increased levels of Egr-1 can speed up wound healing.

In some cases, it may be desired to reduce the level of shear stress responsiveness. For example, it may be desired to slow down the treatment of wounds by this route (possibly in order to reduce scarring). Alternatively it may be desired to reduce the risk of cardio-vascular problems associated with shear stress responsiveness.

The tenth aspect of the present invention is also useful here. It provides for the first time the full sequences of five human SREs associated with the regulation of human Egr-1 transcription. One or more of these may be mutated to reduce the level of shear stress responsiveness relative to that obtainable using one or more of the SREs shown in FIG. 7 for GW SEQ.

In other cases, it may be desired to increase the level of shear stress responsiveness by providing mutations in one or more of the five SREs so as to increase the level of shear stress responsiveness relative to that obtainable using the SREs shown for GW SEQ in FIG. 7. Such mutations may for example be useful in speeding up the treatment of wounds.

Nucleic acid molecules of the tenth aspect of the present invention may be in the form of vectors, although this is not essential. They may be administered to a patient by physical methods. Such methods include topical application of the 'naked' nucleic acid vector in an appropriate vehicle—for example in solution in a pharmaceutically acceptable excipient such as phosphate buffered saline (PBS). Such methods include particle bombardment (which is also known as 'gene gun' technology and is described in U.S. Pat. No. 5,371,015. Here, inert particles, such as gold beads coated with nucleic acid are accelerated at speeds sufficient to enable them to penetrate the surface at the wound site (e.g. skin) by means of discharge under high pressure from a projecting device (particles coated with a nucleic acid molecule of the present invention are within the scope of the present invention, as are devices comprising such particles). Other physical methods of administering the DNA directly to a recipient include ultrasound, electrical stimulation, electroporation and microseeding. Particularly preferred is the microseeding mode of delivery. This is described in U.S. Pat. No. 5,697,901.

Nucleic acid molecules of the tenth aspect of the invention may also be administered by means of specialised delivery vectors.

Any vector suitable for gene therapy can be used. Gene therapy approaches are discussed for example by Verna et al in *Nature* 389:239–242. Both viral and non-viral systems can be used.

Viral based systems include retroviral, lentiviral, adenoviral, adeno-associated viral, herpes viral and vaccinia-viral based systems.

Non-viral based systems include direct administration of nucleic acids and liposome-based systems.

A nucleic acid sequence of the tenth aspect of the present invention may even be administered by means of transformed host cells. Such cells include cells harvested from a subject. The nucleic acid molecules of the present invention can be introduced into such cells in vitro and the transformed cells can later be returned to the subject. The nucleic acid molecules need not be introduced as vectors since non-vector nucleic acid molecules can be introduced. Some such molecules may integrate into nucleic acid already present in the host cell by homologous recombination events.

The present invention also includes within its scope expression systems that can be used to provide polypeptides (e.g. Egr-1). Such polypeptides may then be used in therapy.

Preferred expression vectors are eukaryotic vectors. However prokaryotic vectors can also be used. Suitable vectors will generally include a coding sequence operatively linked to one or more regulatory sequences. Preferably, the coding sequences encode Egr-1.

Many different expression systems are known and are discussed, for example in Sambrook et al (*Molecular Cloning*, 2nd Edition, Cold Spring Harbor Laboratory Press (1989)).

It will be appreciated from the foregoing discussion that nucleic acids of the tenth aspect of the present invention (which may be present in the form of vectors) can be used in various therapeutic applications, as can polypeptides produced using such nucleic acids. The present invention therefore includes within its scope pharmaceutically acceptable compositions comprising said nucleic acids or polypeptides, optionally in combination with a pharmaceutically acceptable carrier or carriers.

Such carriers may include, but are not limited to saline, buffered saline, dextrose, water, glycerol, ethanol and combinations thereof.

Polypeptides and nucleic acids may be employed in the present invention may alone or in conjunction with other substances, such as therapeutic substances. For example Egr-1 repressors may be administered (such as NAB1 and/or NAB2) in certain circumstances (e.g. if it is desired to minimise scarring, to inhibit resteriosis, to modulate vessel wall calcification and/or to inhibit cell proliferation (e.g. in cancers)). Where two or more active agents are to be administered this may be done as a combined preparation for simultaneous, separate or sequential use.

Pharmaceutical compositions of the present invention may be administered in any effective manner including, for instance, administration by topical, intravenous, intramuscular, intranasal or intradermal routes among others. Generally it is preferred that the compositions will be locally applied—e.g. at or close to a wound site or associated condition. However systemic administration may be used.

An active agent may be administered to an individual as an injectable composition, for example as a sterile aqueous dispersion. This is preferably substantially isotonic with a patient's body fluids (e.g. with blood from the patient).

Alternatively the composition may be formulated for topical application for example in the form of ointments, creams, lotions, eye ointments, eye drops, ear drops, mouthwash, impregnated dressings and sutures and aerosols. It may contain additives, including, for example, preservatives, solvents to assist drug penetration, and emollients in ointments and creams. Such topical formulations may also contain compatible carriers, for example cream or ointment bases, and ethanol or oleyl alcohol for lotions. Such carriers may constitute from about 1% to about 98% by weight of the formulation. More usually they will constitute up to about 80% by weight of the formulation.

Most preferably, pharmaceutical compositions comprising nucleic acids of the present invention are adapted for administration by "gene gun" technology. Thus the nucleic acids may be associated with particles (e.g. gold beads) that can be used as projectiles.

For administration to mammals, and particularly humans, it is expected that the daily dosage level of an active agent will be from 0.01 mg/kg to 10 mg/kg, typically around 1 mg/kg. In practice, a physician will determine the actual dosage that will be most suitable for an individual and this may well vary with the age, weight and condition of the particular individual. If side effects develop, the dosage can be reduced in accordance with good clinical practice.

In addition to therapeutic uses, the present invention may also be used in diagnosis. As discussed above, the present invention provides probes that can be used in the diagnosis of various disorders. These may be provided as part of a diagnostic kit that may include other components—e.g. one or more washing liquids, means for detecting hybridisation, instructions for use, etc. The probes may be labelled with a detectable label (e.g. a fluorescent label or a radio-label).

The present invention may be used in screening. For example a nucleic acid molecule of the tenth aspect of the present invention (such as a molecule comprising the GW SEQ shown in FIG. 7 or part thereof) may be used to screen for substances that bind thereto. Such substances can be assayed to see if they affect the transcription of Egr-1. Thus they may be useful in designing medicaments for the treatments discussed above. Alternatively a nucleic acid molecule of the tenth aspect of the present invention may be used to screen for a substance capable of blocking the binding of another substance to the nucleic acid molecule. If the other substance is a regulator of the transcription of Egr-1, substances blocking said binding can also be useful in designing medicaments for use in one or more of the treatments discussed above.

The present invention may be used in research. For example nucleic acid molecules of the tenth aspect of the present invention may be used as a starting point in studies whereby one or more changes are made relative to a given nucleic acid molecule. This can be done to determine which parts thereof are important in the transcription of Egr-1 or are important in the regulation of such transcription. For example insertions/deletions/ replacements may be made relative to one or more of boxed regions shown in FIG. 7 for GW SEQ and the effect of such insertions/deletions/ replacements may then be investigated. Changes may be made to try to identify nucleic acid molecules capable of providing increased or reduced levels of transcription of Egr-1.

Preferred features of each aspect of the invention are as for each of the other aspects *mutatis mutandis*. The prior art documents mentioned herein are incorporated to the fullest extent permitted by law.

The present invention will now be described by way of example only with reference to the accompanying figures, wherein:

BRIEF DESCRIPTION OF THE DRAWINGS

FIGS. 1a and b show Egr-1 expression of VEGF;

FIG. 1c and d show Egr-1 expression of TGF-B1;

FIG. 1e and f show Egr-1 expression of PDGF A;

FIG. 4a shows the samples for bone loading using western blot analysis;

FIG. 4c shows an ELISA analysis of PDGF BB produced from TE85 bone cells after exposure to load;

FIG. 4d shows the detection of VEGF and TGF-B1 after transfection of CMV-TGF-B1 in ROS cells;

FIG. 4e shows detection of VEGF and TGF-B1 after transfection of of CMV-TGF-B1 in MC3tE1 cells;

FIG. 5 shows effect of Egr-1 on alkaline phosphatase levels in a rodent model of ectopic bone formation;

FIG. 6a shows anti-Egr-1 antibody staining of human smooth muscle cells transfected with CMV Egr-1;

FIG. 6b shows anti-Egr-1 antibody staining of porcine smooth muscle cells transfected with CMV Egr-1 DNA;

FIG. 7 shows a comparison of two nucleotide sequences indicated as GW SEQ and ON SEQ respectively. ON SEQ (SEQ ID NO:2) is the published early growth response-1 promoter (Sakamoto et al Oncogene 6; 867–871, 1991), and GW SEQ (SEQ ID NO:3) is a sequence in accordance with the invention, which contains a number of base insertions/ deletions as shown and substitutions (bold-underlined).

FIG. 8 shows a variant of the sequence shown in FIG. 7, which variant (SEQ ID NO:4) has a modified EBS region Mutation in the Egr-1 binding site (EBS) is shown in bold-underline.

FIG. 9 shows the published 5' upstream sequence (SEQ ID NO:1) of mouse Egr-1 gene (Morris, Nucleic Acids Research, 16: 8835–8846). The nucleotides are numbered from the cap site =+1. Putative TATA and CCMT elements are boxed. Potential regulatory elements are underlined and indicated in the figure. Dotted underline shows position of 29-mer used for primer extension studies.

FIG. 10 shows activation of SRE5 by transient transfection of pFA-MEK1.

EXAMPLES

Figure 2A:
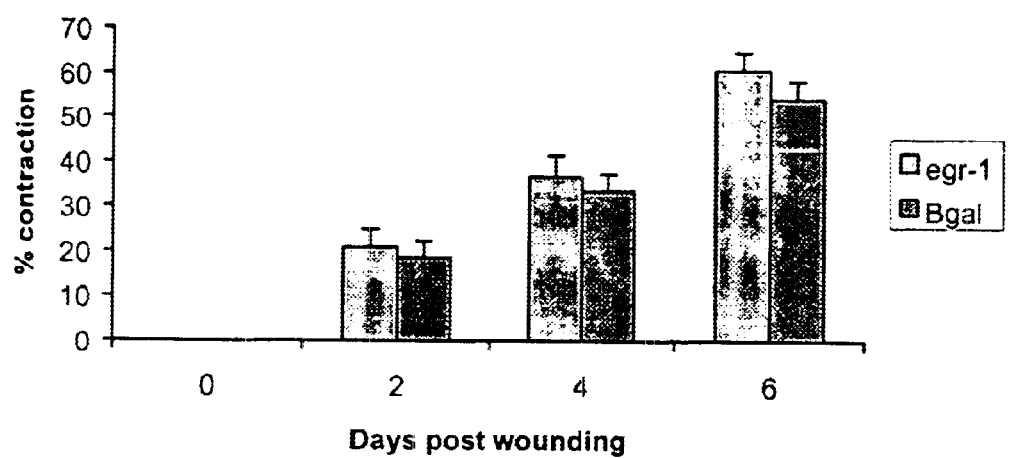
FIG. 2a shows the effect of Egr-1 on rat excisional wound contraction.

Examples 1 and 2 describe gene gun delivery of β-galactosidase and Egr-1 expression plasmid DNAs, complexed to gold particles, to rodent skin.

a) Preparation of Tubing Station

The tubing preparation equipment was set up in a sterile air laminar flow cabinet, and swabbed with 70% I.M.S. and air dried in the cabinet. Gas line tubing from the nitrogen cylinder to the tubing preparation equipment was autoclaved and a Gelman in-line 0.2 μm filter attached. The autoclaved tubing was connected to the gas inlet on the preparation equipment by a luer lock connector, and gas allowed to flow through at 0.2 litres/minute to dry the tubing completely.

The particle delivery tubing was attached to the preparation equipment and gas allowed to flow through as above to completely dry the interior of the tubing. Any residual moisture in the tubing will result in a poor or uneven attachment of the gold particles to the tubing walls and may adversely affect the outcome of any experiment.

b) DNA-gold Microcarrier Bead Preparation:

Gold beads of 1.0 μm were obtained from Bio-Rad UK. An aliquot of gold beads (53 mg) was weighed out into a microfuge tube, and 100 μl of 0.05 M spermidine was added and the tube vortexed gently.

100 μl of DNA solution containing 100–120 μg of plasmid DNA expressing either Egr-1 or β-galactosidase was added followed by 100 μl of 1M $CaCl_2$ added dropwise while vortexing. This mixture was left to stand for 10 minutes at room temperature then spun down. The supernatant was removed and the gold pellet was washed three times in absolute EtOH.

The gold particles were finally resuspended in absolute ethanol containing 0.1 mg/ml polyvinyl pyrrolidone (PVP).

Estimation of coating efficiency of DNA to gold microcarriers, and release in aqueous solution: All samples (starting material, post-precipitation supernatant following DNA/gold complex formation, and eluted material) were assayed for DNA in a "GeneQuant" (Pharmacia). The residual post-precipitation DNA gave a measure of unbound material, and the ratio of bound: starting material was deemed to be the coating efficiency.

c) Loading the DNA/microcarrier Suspension Into the Gold Delivery Tubing:

The gold particle suspension in ethanol/PVP was then loaded into the delivery tubing using a syringe, and the suspension allowed to stand for 3–5 minutes in the tubing. During this time the particles precipitated on the inner face of the tubing allowing the ethanol to be removed by the syringe. When the ethanol had been removed, the tubing was rotated to distribute the gold particles evenly on the inner face of the tubing. After 2–3 minutes rotation, nitrogen gas was passed through the tubing at a rate of 0.1 litres/minutes to remove residual ethanol and allow the gold particles to adhere. After 10 minutes, the tubing was removed, cut into appropriate lengths using the cutter provided (Bio-Rad UK), and the cut tubing was loaded into the gene gun.

Egr-1 expression and activity was determined using standard immunohistochemistry with commercially available antibody preparations for detection of Egr-1 (Santa Cruz), and Egr-1 target gene products (Santa Cruz or R&D systems) and expression was monitored from 1–7 days. The negative control was null DNA.

Example 1

Delivery of Egr-1 DNA to Unwounded Rodent Skin 1.1 Methods

An expression plasmid comprising the Egr-1 cDNA driven from the human cytomegalovirus promoter (hCMV; Houston et al, Arterioscler. Thromb. Vasc. Biol., 19; 281–289, 1999) was delivered to the backs of unwounded mice via gene gun mediated particle delivery. Gold/DNA complexes were prepared as described above and 0.5–1.0 μg DNA was delivered per animal using a gene gun pressure of 350 psi and a gold particle size of 1.6 microns. Animals were sacrificed at day 0, 1, 2 and 6 days post delivery of DNA and the skin was embedded in OCT and snap frozen in dry ice/hexane. Sections were prepared at 0.7 μm and Egr-1 target growth factors examined by immunostaining using antibodies directed against VEGF, PDGF A, TGFβ and Egr-1.

1.2 Results

Immunohistochemical data is shown for Egr-1 activation of VEGF (FIG. 1a. and 1b.), TGFβ (FIG. 1c. and 1d.) PDGF A (FIG. 1e. and 1f.). Results show dramatic upregulation of VEGF protein at days 1 and 2, declining at day 6, upregulation of TGFb at day 6 but not at days 1 and 2 and rapid up-regulation of PDGF A at 2 hrs post Egr-1 DNA delivery (designated day 0).

1.3 Conclusion

These data confirm that Egr-1 can activate the expression of target growth factors in vivo, some of which are described herein. These data illustrate that Egr-1 activation of growth factors occurs over a temporally separate timescale.

Having confirmed activation of Egr-1 target genes using unwounded rodent skin(Example 1), Egr-1 and β-galactosidase gene gun delivery of excisional rat wounds was performed to assess the effect of Egr-1 on the rate of healing.

Example 2

Use of Egr-1 Transcription Factor to Promote Wound Repair in Rodents 2.1 Methods 2.1.1 Plasmid constructs:

The expression plasmids used in this study were CMV driven β-galactosidase and CMV driven Egr-1 (Houston et al, Arterioscler. Thromb. Vasc. Biol, 19; 281–289, 1999). Plasmids were propagated in *Eschericia coli* XL-2 Blue MR and DNA was prepared using Qiagen maxi kits.

2.1.2 Particle Mediated Gene Transfer:

Eighteen male Sprague Dawley rats weighing 250g were anaesthetised under isoflorane in a 2:1 mixture of oxygen/nitrous oxide. Two sites of transfection (8 cm from the skull, 1.5 cm either side of the spine) on the rat dorsum were prepared by firstly clipping the pelt then shaving with a razor. Two transfections were carried out per wound site, 8 mm apart, by accelerating plasmid/gold complexes of either Egr-1 or β-galactosidase into the skin at 350 psi. Total amount of DNA was not less than 1.7 μg per transfection (equalling 3.4 μg per wound).

2.1.3 Excisional Wound Healing Model:

Twenty-four hours post transfection animals were anaesthetised and 2 full thickness excisional wounds made (8 mm diameter) using a biopsy blade at the exact sites of transfection (see below). Immediately after wounding each wound was captured using camera/video set up and the animals allowed to recover from anesthesia. At 2, 4 and 6 days post wounding 6 animals were killed and each wound captured again using the same camera/video set up. Following capture, the wounds were dissected out and harvested for routine histology and immunohistochemistry.

2.1.4 Healing Analysis:

i) Macroscopic Assessment

Wound area was determined using image analysis and the healing expressed as a increase in percent of original wound area. Statistical significances of differences between treated and control groups were evaluated using a paired Mann-Whitney test.

ii) Microscopic Assessment

Histological Analysis:

Each wound per time point after dissection was bisected horizontally. One half was placed in 4% paraformaldehyde for 24 hours and processed for wax histology. 5 μm sections from each wound were cut using a microtome and the sections stained with van Geison. Using this histological stain, key markers of wound healing was assessed including re-epithelialisation and collagen content and comparisons made between treated and control sections.

Immunocytochemistry:

Immunocytochemistry and image analysis was performed in order to quantify the differences seen using routine histology. Once frozen in OCT, the second half of each wound was sectioned at 7 μm using a cryotstat. Two sections from each wound were fixed in ice-cold acetone and fluorescent immunostaining was performed with primary's to collagen I and von Willebrand factor (vWF). Immediately after immunostaining each slide was placed under a fluorescent microscope and the wound area captured using a ×25 magnification. The image was intergrated and a threshold set to minimise backround. Area and intensity of staining was measured using image analysis and plotted as a graph. Statistical significant differences between treated and control groups were evaluated using a Man-Whitney nonparametric test.

2.2 Results 2.2.1 Effect of Egr-1 on rat excisional wound healing (i) Wound Contraction:

Full thickness rat dermal excisional wounds 8 mm in diameter contracted marginally faster in response to Egr-1 transfection compared to control (β-galactosidase) up to 6 days post wounding. Statistically significant enhancements of contraction (p<0.05) occurred at 6 days post wounding where Egr-1 treated wounds contracted to an area 7% smaller than control (FIG. 2a.).

Figure 2B:
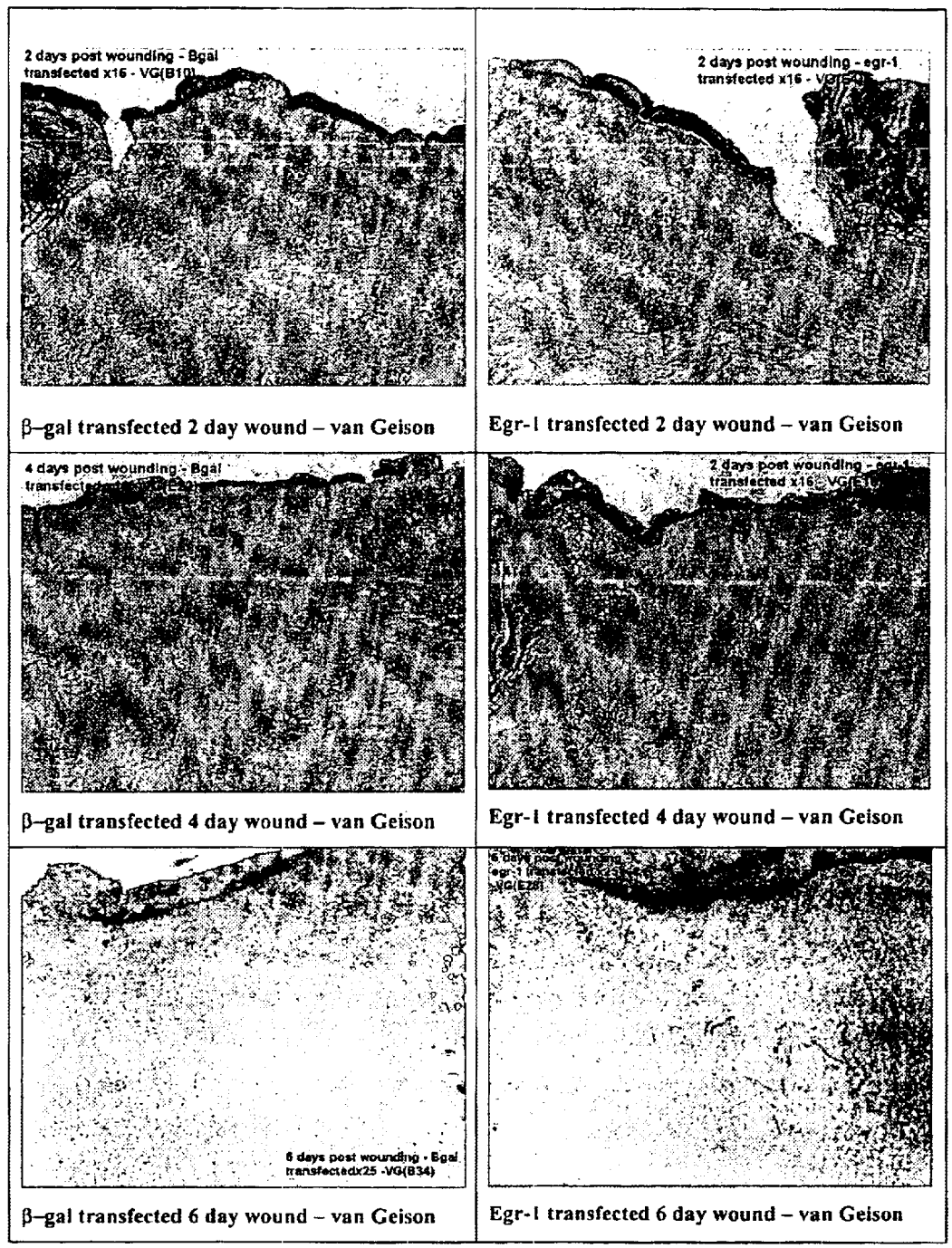
FIG. 2b shows the effect ogf Egr-1 DNA transfection on the histology of healing rat excisional wounds.

(ii) Histological Analysis:

Wounds sections stained with van Gieson showed marked differences in the histology of wounds at 4 and 6 days post wounding. At 2 days post wounding there was little difference between Egr-1 and β-galactosidase transfected wounds. Both treatments showed mononuclear cells at the wound site indicating the early inflammatory response, with early scab formation, but no re-epithelialisation. At 4 days post wounding re-epithelialisation had still not commenced, however wounds transfected with Egr-1 had more collagen within the wound site compared to β-galactosidase. At 6 days post wounding wounds treated with Egr-1 had a more mature granulation tissue showing markedly more collagen within the wound site compared to β-galactosidase, to an extent where clear thick collagen fibres could be seen. Re-epithelialsation was complete in 50% of wounds treated with Egr-1 compared to 0% in β-galactosidase. Histologically Egr-1 treated wounds showed accelerated healing compare to β-galactosidase (FIG. 2b.).

Figure 2C:
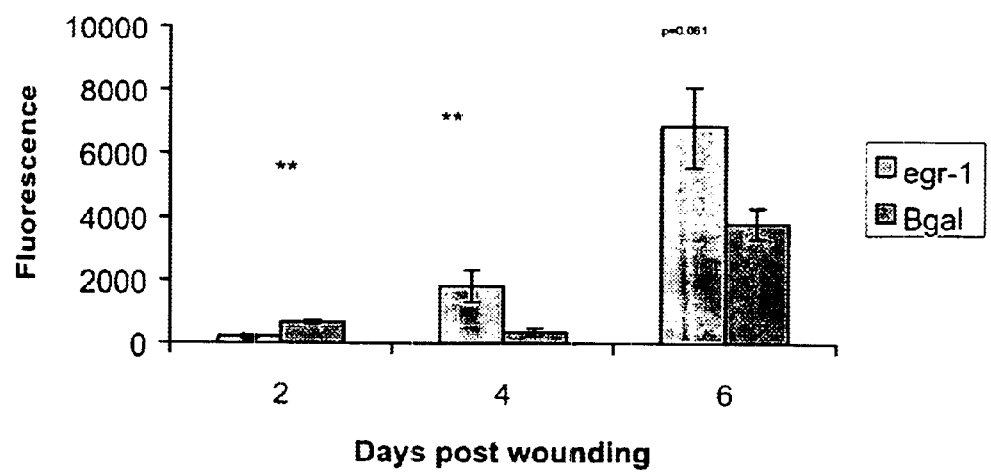
FIG. 2c shows the effect of Egr-1 on collagen deposition on rat excisional wounds.

(iii) Quantification of the Effect of Egr-1 on Collagen Deposition Using Immunohistochemistry and Image Analysis:

Collagen I immunostaining was performed on 7 μm crytosections of wounds treated with Egr-1 or β-galactosidase and the staining quantified using image analysis. Wounds treated with β-galactosidase had significantly more collagen at 2 days post wounding compared to Egr-1. At 4 and 6 days post wounding Egr-1 transfected wounds had more collagen deposition than control (β-galactosidase) which confirms the findings seen using routine wax histology. Egr-1 transfection increased the amount of collagen deposition at 4 and 6 days post wounding (FIG. 2c.).

Figure 2D:
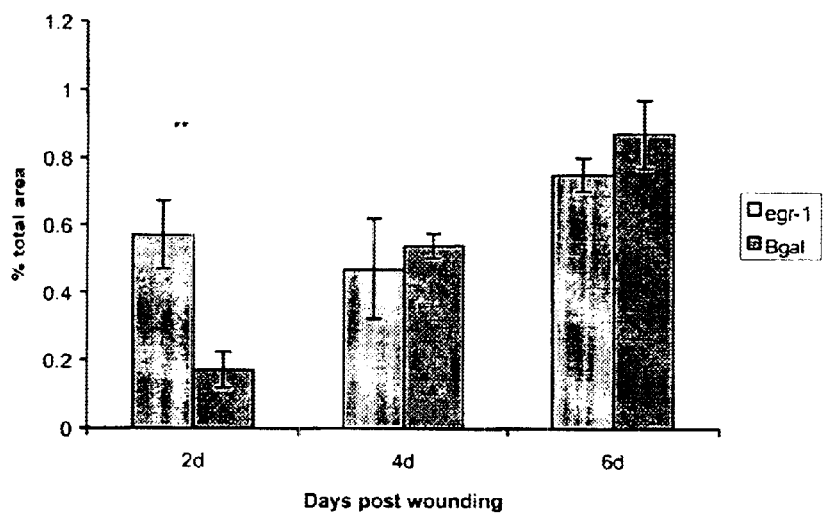
FIG. 2d shows the effect of Egr-1 on the angiogenic profile in rat excisional wounds using vWF immunostaining.

(iv) Quantification of the effect of Egr-1 on angiogenesis using immunohistochemistry and image analysis:

Angiogenesis was quantified using von Willebrand factor immunostaining on wound cryosections and image analysis to measure the area of positive staining within the wound site. At 2 days post wounding Egr-1 transfected wounds had significantly (p<0.01) more new blood vessels compared to control (β-galactosidase). At 4 and 6 days post wounding both Egr-1 and β-galactosidase transfected wounds had similar levels of angiogenesis. Transfection of Egr-1 expressing DNA promoted angiogenesis 2 days earlier than control (FIG. 2d.)

2.3 Conclusions

Egr-1 transfection of rat excisional wounds accelerated healing by increasing the rate of contraction, re-epithelialisation and collagen deposition. Egr-1 transfection also promoted angiogenesis at 2 days post wounding.

Example 3

Use of Egr-1 Transcription Factor to Promote Angiogenesis 3.1 Methods

Egr-1 under the control of the hCMV promoter (Houston et al, Arterioscler. Thromb. Vasc. Biol., 19; 281–289, 1999) was transfected into a human cell co-culture system designed to measure angiogenesis in vitro. The angiogenesis kit (TCS Biologicals) was used as described according to the manufacturer's instructions using VEGF protein (2 ng/ml) and suramin (20 μM) as positive and negative controls respectively for angiogenesis.

Figure 3A:
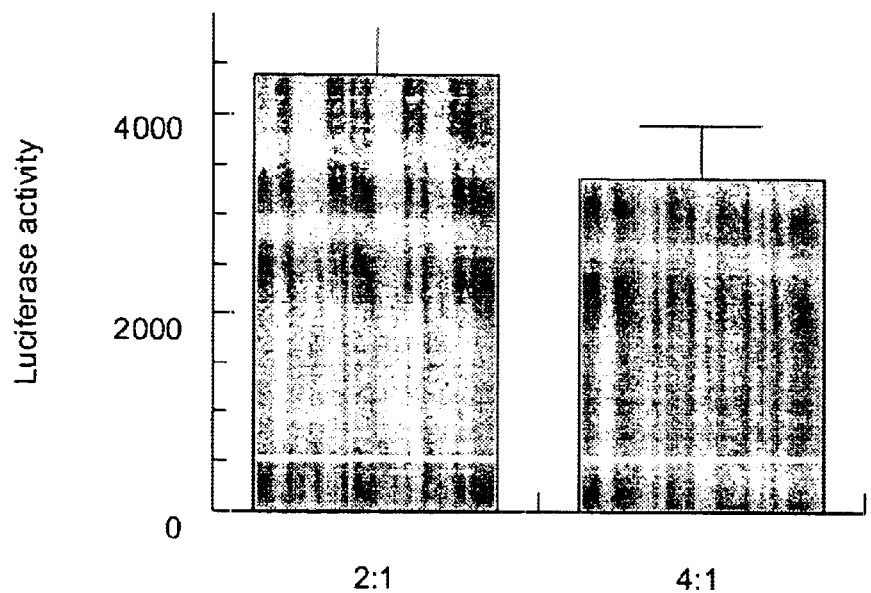
FIG. 3a shows the optimisation of lipid: DNA ratio (v/w) for transfection of pGL3 luciferase control plasmid intothe angiogenesis co-culture system using Mirus TransIT (Cambridge Bioseciences)

Optimisation of transfection in the co-culture system was performed using pGL3 control luciferase (Promega) with 1.0 μg and 0.5 μg CMV-β, gal as a normalising plasmid for transfection control. Two ratios of lipid: DNA (v/w) were used; 2:1 and 4:1 (FIG. 3a.). CMV Egr-1 DNA was transfected at 0.5, 1.0, 1.5 and 2.5 µg per well in triplicate in a 24 well microtitre plate using Mirus Transit reagent (Cambridge Biosciences) at a ratio of 2:1 v/w DNA. VEGF protein positive control and suramin negative control was added to triplicate wells. After 11 days co-culture angiogenesis was determined by staining of cells for the endothelial cell marker PECAM-1 and visualisation using BCIP/NBT substrate.

Representative images of tubule formation using all four doses of Egr-1 expression plasmid together with VEGF (positive control) and suramin (negative control) were captured and processed by image analysis using Quantimet 600 image analyser and associated software.

3.2 Results

Figure 3B:
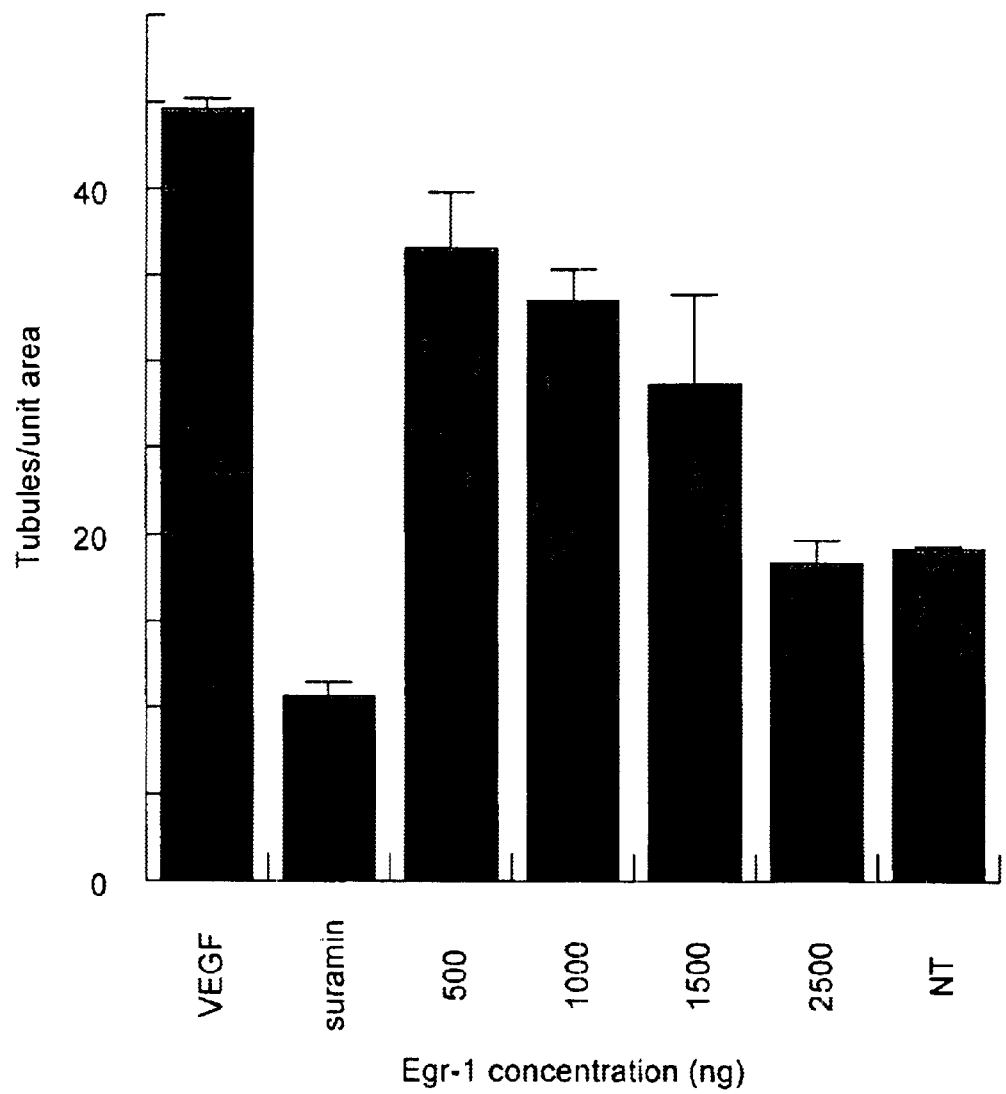
FIG. 3b shows the effect of Egr-1 on angiogenesis.

Angiogenesis as described by tubule formation visible under the light microscope was detectable after 11 days of co-culture. Angiogenic scoring is presented using image analysis as illustrated of the entire well and results are presented as tubules per unit area versus treatment (FIG. 3b.).

Decreased tubule formation (cells treated with suramin and increased tubule formation (cells treated with VEGF protein are shown. Egr-1 was shown to promote enhanced tubule formation in an inverse dose dependent fashion.

3.3 Conclusions

In the co-culture system, Egr-1 transcription factor expression is angiogenic. This supports and is supported by data from Example 1, whereby Egr-1 was shown to upregulate growth factor expression (e.g VEGF) when delivered by gene gun into mouse skin and data from Example 5, where transfection of Egr-1 was shown to increase the amount of VEGF produced in human vascular smooth muscle cells. The inverse dose response of Egr-1 as a pro—angiogenic stimulus is consistent with results obtained in Example 6 and with the notion that Egr-1 may down-regulate it's own production (Cao, X. et al, J. Biol. Chem., 268; 16949–16957, 1993; Schwachtgen, J.-L. et al, J. Clin. Invest., 101, 254–2549, 1998).

Example 4

Use of Egr-1 Transcription Factor to Promote Osteogenesis in Vitro 4.1 Bone Loading and Determination of Growth Factors 4.1.1 Methods:

Cells used were TE85, a human osteosarcoma-derived osteoblast-like cell line. Sub-confluent cell layers were typsinised and resuspended in DMEM containing 10% foetal calf serum (FCS) and 1% penicillin-streptomycin (PS) antibiotics. The cell suspension was seeded onto the loading substrate (18×18 mm squares of tissue culture-treated plastic). Cells were left overnight to attach. Once attached the loading substrates and attached cells were transferred into flasks containing DMEM with 2% FCS and 1% PS for a further 24 hr prior to load stimulation.

There were four sets of conditions for each time point described in FIG. 4a.:

[1]. Load (200 cycles of 2000 microstrain at 3232 microstrain per second).
[2]. Control (no load).
[3]. Positive control (100 ng/ml PMA for 1 hr).
[4]. Solute control.

For cell loading, cells were aseptically transferred from standard tissue culture conditions into the loading chamber. The duration of loading the cells in the chamber was 4 minutes. After loading, cells were then returned to their former culture conditions. Control treated cells were treated in exactly the same way except that no load was applied to the chamber.

Figure 4B:
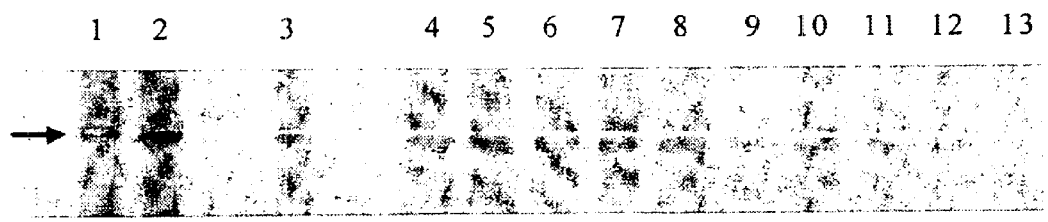
FIG. 4b shows the western blot analysis of Egr-1 protein in human TE85 bome cells exposed to load.

Results were analysed by two different methods. First, the presence of the Egr-1 transcription factor was determined by Western blot analyses of cell pellets collected after the loading experiments (FIG. 4b). Secondly, the presence of secreted growth factors was determined by ELISA assay of tissue culture 35 medium (FIG. 4c).

4.1.2 Conclusions:

These results show under conditions of bone loading that the transcription factor Egr-1 is produced in human osteosarcoma-derived osteoblast-like cells. Application of bone loading to human TE85 cells stimulates the production and secretion of growth factors, an example of which is PDGF B.

4.2 Transfection of CMV TGF-β1 into MC3T3E1 and ROS Cells Followed by Human TGF-β1 and Mouse VEGF ELISA Assays of Cell Culture Supernatents.

4.2.1 Materials:

(i) Transfection

Mouse Osteoblast cells (MC3T3E1) and rat Osteosarcoma cells (ROS17/2.8) were used seeded in 6 well plates.

MC3T3E1 cells were cultured in MEM-α, Minimum essential medium eagle, alpha modification (Sigma), 10% Foetal calf serum (Life Technologies), 1% L-glutamine (Life Technologies), 1% penicillin-streptomycin (Life Technologies).

ROS cells were cultured in F12 HAM, F-12 HAM with glutamine (Life Technologies), 10% Foetal calf serum (Life Technologies), 1% penicillin-streptomycin (Life Technologies).

Cells were transfected using Fugene (Boehringer Mannheim) with a CMV TGF-β1 expressing plasmid as described (Benn, S. 1. et al, J. Clin. Invest., 98; 2894–2902, 1996). Transfection into cells was carried out as described:

1) A six well plate was prepared with 2×10⁵ cells per well and left overnight, until 50–70% confluent.
2) Next day 94 µl of Serum free media (SFM) and 6 µl of Fugene were added to each of 6 eppendorf tubes and left at room temperature for 5 min.
3) To 6 separate tubes, no DNA was added to 2 tubes, while 4pg of CMV-TGF-β1 DNA was added to the remaining 4 tubes.
4) The Fugene/SFM mix from step 2) was added dropwise to the tubes from step
3), the tubes were flicked several times and then incubated for 15 min at room temperature.
5) The Fugene/SFM/DNA transfection mixes were added dropwise to their respective wells, while swirling the 6 well plate, the plate was incubated at 37° C. for 48 hrs.
6) Cell culture supernatents were aliquoted and stored at −20° C. The above protocol was performed for both MC3T3E1 cells and ROS cells. The presence of TGF-β1 and VEGF in the cell culture supernatant was detected by ELISA (R&D Systems) using a streptavidin-HRP based colour detection system.

4.2.2 Results:

Production and detection of TGF-β1 and VEGF following transfection of CMV-TGF-β1 is shown in ROS cells (FIG. 3) and MC3T3E1cells (FIG. 4). These data show that an Egr-1 target gene, in this example TGF-β1 have activate the production of VEGF.

4.3 Conclusion

Expression of Egr-1 and activation of Egr-1 target genes may synergistically activate VEGF.

Example 5

Use of Egr-1 Transcription Factor to Promote Osteogenesis in Vivo 5.1 Rat Ectopic Bone Formation Subcutaneous implantation of possible bone inducing compounds in rodents represents the most extensively studied biological assay system in current use (Wozney, J. M., Cell. Mol. Biol., 131–167, 1993). The use of a carrier matrix enhances the reproducibility and sensitivity of the bone induction response. In this assay system (Reddi, A. H. et al, Proc. Natl. Acad. Sci. USA, 69; 1601–1605, 1972; Sampath, T. K., ibid, 78; 7599–7603, 1981) the carrier matrix is derived from the diaphyseal portion of rat long bones that have been ground into particles of a particular size , subsequently demineralised and biological activity removed by guanidine extraction. The remaining carrier consists primarily of bone collagen with no osteoinductive capacity. The compound or substance to be assayed is then deposited onto the matrix by precipitation with alcohol, dialysis against water or lyophilisation. This matrix combination is then implanted into the subcutaneous tissues of the rat for a number of days (12 days in this experiment). The implants are then assayed histologically and biochemically for their ability to induce bone formation (Sampath, T. K. et al, Proc. Natl. Acad. Sci. USA, 80; 6591–6595, 1983; Sampath, T. K. et al, ibid, 84; 7109–7113, 1987; Wang, E. ibid, 85; 9484–9488; Wang, E. et al, ibid, 87; 2220–2224; Sampath, T. K. et al, J. Cell Biol., 98; 2192–2197, 1984).

5.1.1 Experimental Methods:

Prep Twenty male Sprague Dawley rats (age 4249 days, weight 170–220g) were randomly allocated to receive two implants inserted subcutaneously over the dorsal thorax under halothane anesthesia. The implants comprised one of four treatments:

Negative control—Carrier alone (demineralised guanidine extracted bone matrix DGBM)

CMV Egr 1 DNA; 500ug on carrier DGBM

CMV Egr 1 DNA; 500ug plus recombinant bone morphogenetic protein (BMP) 4; 5ug on carrier DGBM, (BMP4 being used for its chemotactic effects)

Recombinant BMP4 Protein 5ug on carrier DGBM

The day of insertion was regarded as day 0 and on day 12 post operatively all rats were killed using a schedule 1 approved method, the implants were removed, cleaned of soft tissue and divided into equal halves. One half was placed in 10% formalin for histological examination and the other half was frozen and stored at −20 degrees centigrade. This sample was then assayed for calcium content and alkaline phosphatase activity.

5.1.2 Preparation of demineralised rat bone:

The diaphyseal shafts of the femora, tibiae and humeri of adult Sprague Dawley rats were removed, stripped of soft tissue and the marrow cavities irrigated with normal saline. The bone was then defatted by stirring in 100 ml Chloroform:Methanol (2:1} for 30 min. This step was repeated once prior to air drying in a drying oven. The bone shafts were then frozen in liquid nitrogen and pulverised in a CRC micromill. The resultant powder was sieved to leave a discreet particle size of 75–425 um and then demineralised in 0.5 HCl for 3 hours with constant stirring. The mixture was then centrifuged for 30 minutes at 19,0000 rpm (Kontron CentriksT124, Rotor A8.24) at 15 degrees centigrade. The pellet was resuspended in 100 ml water stirred for one hour and centrifuged. This step was then repeated. The pellet was then resuspended in 100 ml ethanol stirred for one hour and centrifuged. The ethanol was evaporated off and the sample resuspended in 4M guanidine hydrochloride/50 mM Tris, pH7.4 and stirred overnight. Further centrifugation was then carried out with the pellet resuspended in 50 ml water stirred for one hour and centrifuged. This step was repeated a further two times. The sample was then dried overnight in a drying oven. DNA was added to bone by mechanical mixing and lyophilisation.

5.2 Histological Examination

After initial fixation in formalin, the samples were embedded in methyl methacrylate and 1 μm sections cut and stained with Von Kossa and Toluidine Blue. Three nonadjacent sections from each implant were then evaluated by a consultant histopathologist blinded to the test substance and the scores averaged.

A standard scoring system for cartilage and bone was used; +/− tentative identification of bone or cartilage
1. >10% each section new cartilage or bone
2. >25% each section new cartilage or bone
3. >50% each section new cartilage or bone
4. >75% each section new cartilage or bone
5. >80% each section new cartilage or bone 5.3 Biochemical Testing The tissue was homogenized in 2 ml of ice cold 0.25 M sucrose- 3mMNaHCO3. The homogenates were centrifuged at 12,000 g for 15 min at 2 degrees centigrade and the supernatants collected for enzyme assays. Alkaline phosphatase activity was determined using a colourimetric assay with p-nitrophenyl phosphate (PNP) as the substrate. After incubation of test samples with PNP at 37 degrees centigrade, optical density was determined at 405 nm in a standard micotitre plate reader.

5.4 Results.

The results are presented in FIG. 5. The data was analysed treating the two implant sites for each rat as independent from one another. Medians and interquartile ranges (IQR) are presented because of the small numbers and the skewed distribution of the data. Kruskal Wallis tests have been carried out on the above variables and found that the alkaline phosphate levels differ significantly from one another.

Bone formation was positive for one implant in five implanted sites in only one group (CMV Egr-1 DNA/BMP). The initial experiment used a single timepoint for assay of 12 days, which was chosen to give early predictive results. At this timepoint levels of alkaline phosphatase activity are significantly elevated in CMV Egr-1 DNA and CMV Egr-1 DNA/BMP4 groups over controls. Such temporal increase in alkaline phosphatase activity is seen typically (as a precursor to bone formation) with substances such as BMP which stimulate bone formation rising to a peak at 10–15 days and falling thereafter. This represents the rise seen in the earliest phase of enchondral ossification. Calcium content does not show significant differences in the samples so far tested although early calcification has been observed in a number of histological samples in the CMV-Egr-1/BMP4 group. This may be explained due to the timescale of biopsy where calcification is only just starting.

5.5 Conclusion

Egr-1 increases alkaline phosphatase levels in a rodent model of ectopic bone formation and may promote localised bone formation.

Example 6

Use of Egr-1 Transcription Factor to Promote Re-endothelialisation After Percutaneous Transluminal Coronary Angioplasty in vitro 6.1 Methods Human or porcine vascular smooth muscle cells (SMC; Clonetics) were thawed, maintained in medium and passaged until no later than passage 4 according to the manufacturer's instructions. SMC were transfected with an expression plasmid comprising the Egr-1 cDNA expressed from the CMV promoter Houston et al, Arterioscler. Thromb. Vasc. Biol., 19; 218–289, 1999). Egr-1 expressing DNA was transfected into SMC using Fugene (Boehringer Mannheim) after optimisation of SMC with the luciferase reporter vector pGL3 control (Promega) or Mirus Transit (Cambridge Biosciences) both transfection protocols used β-galactosidase as a normalising plasmid for transfection control.

6.2 Results

Figure 6C:
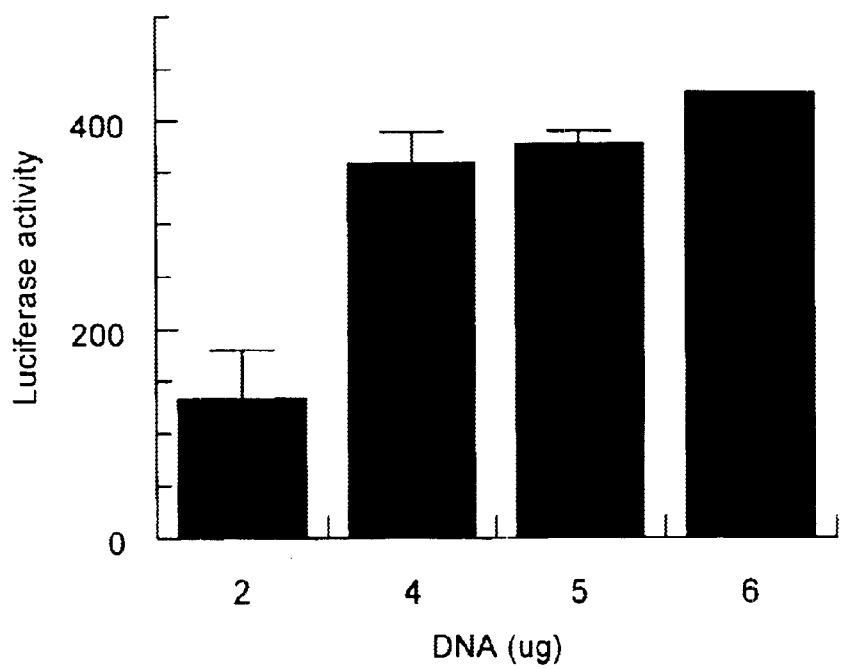
FIG. 6c shows optimisation of transfection of pGL3 luciferase control in human SMC by Fugene.
Figure 6D:
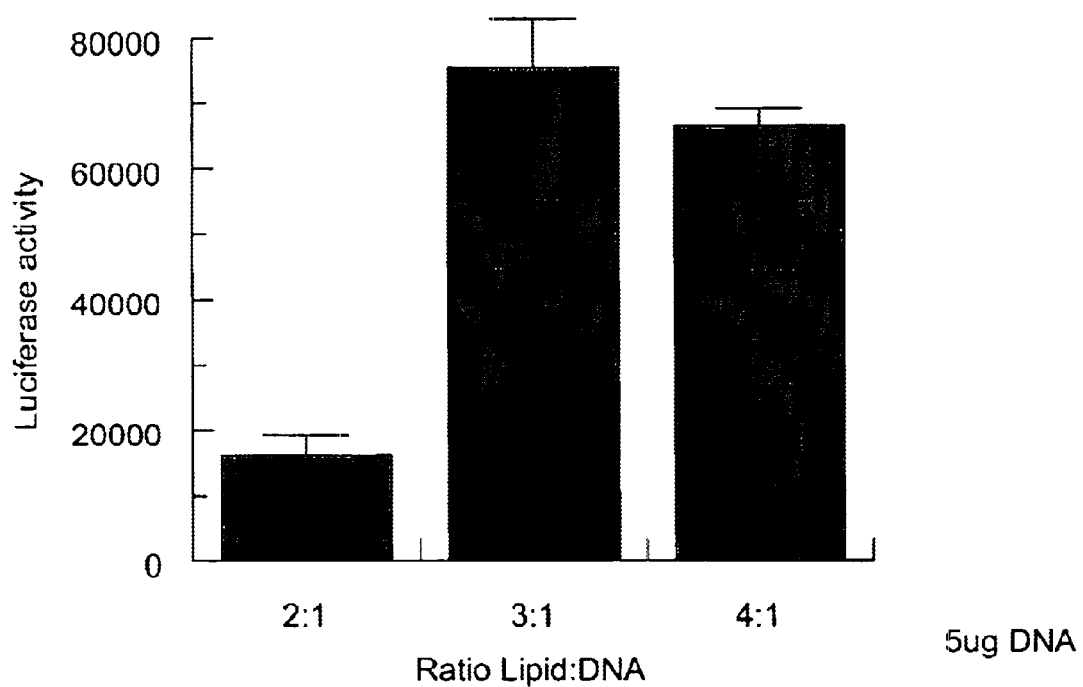
FIG. 6d shows optimisation of transfection of pGL3 luciferase control in porcine SMC by Fugene.

CMV Egr-1 DNA was transfected into human SMC and Egr-1 protein was detected by immunohistochemistry using a polyclonal antibody (Santa Cruz) and peroxidase detection (Sigma and Vector Laboratories). Human SMC transfected with CMV Egr-1 DNA (right hand panel) or mock transfected (left hand panel) are shown in FIG. 6a., and porcine SMC transfected with CMV Egr-1 DNA (right hand panel) or mock transfected (left hand panel) are shown in FIG. 6b. Egr-1 protein expression is detectable as brown staining. Optimisation of DNA transfection was achieved using Fugene 6 (for further in vitro characterisation, FIG. 6c.) and Mirus Transit (for subsequent in vivo studies, FIG. 6d.). From these data, 4 μg CMV-Egr-1 DNA was used routinely for growth factor activation experiments using a lipid:DNA ratio of 3:1. A lipid:DNA ratio of 3:1 was also used for in vivo gene delivery experiments.

Figure 6E:
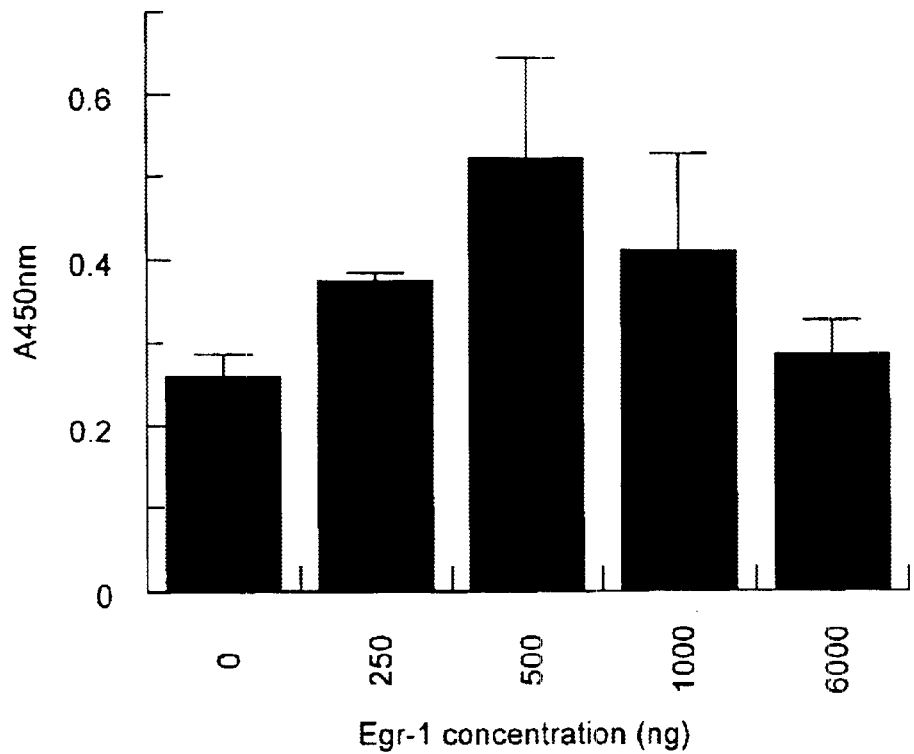
FIG. 6e shows activation of VEGF production/secretion by transfection of CMV-Egr-1 into human SMC.
Figure 6F:
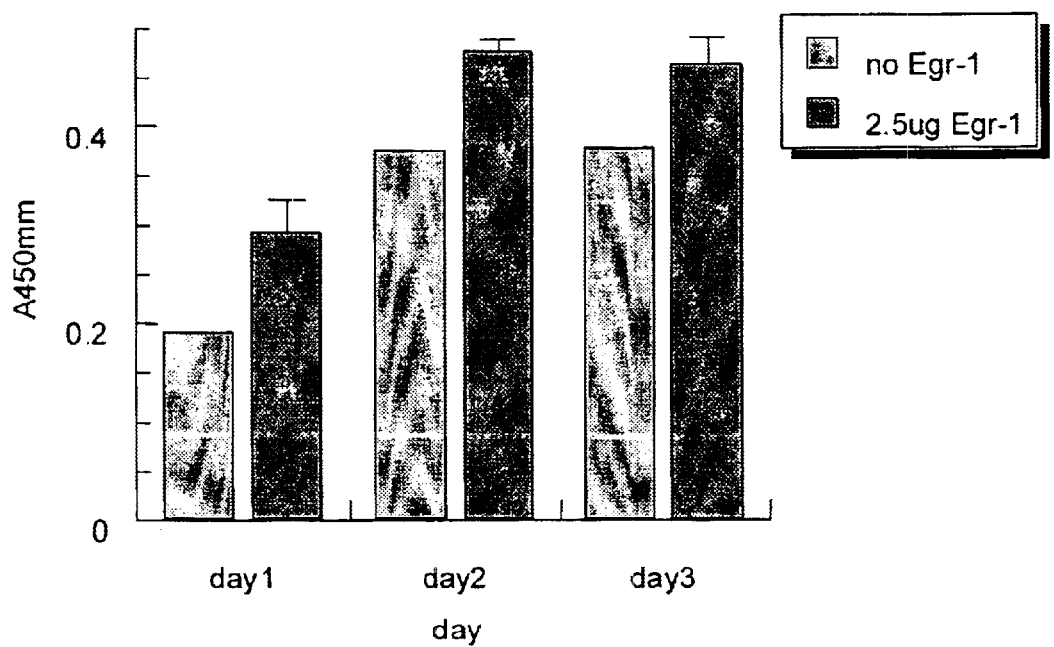
FIG. 6f shows activation of HGF production/secretion by transfection of CMV-Egr-1 into human SMC.
Figure 6G:
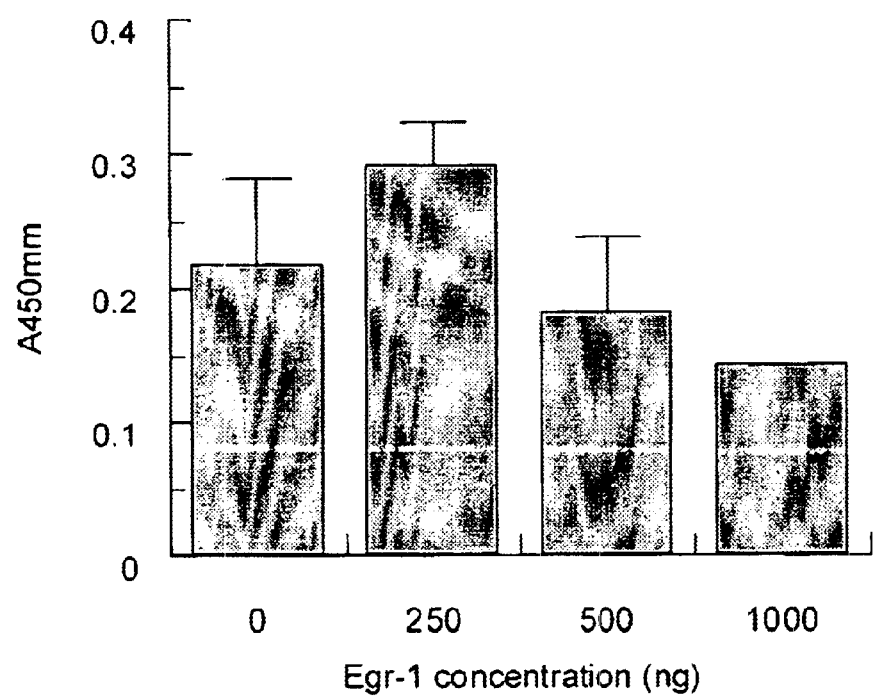
FIG. 6g shows activation of PDGF production/secretion by transfection of CMV-Egr-1 into human SMC.
Figure 6H:
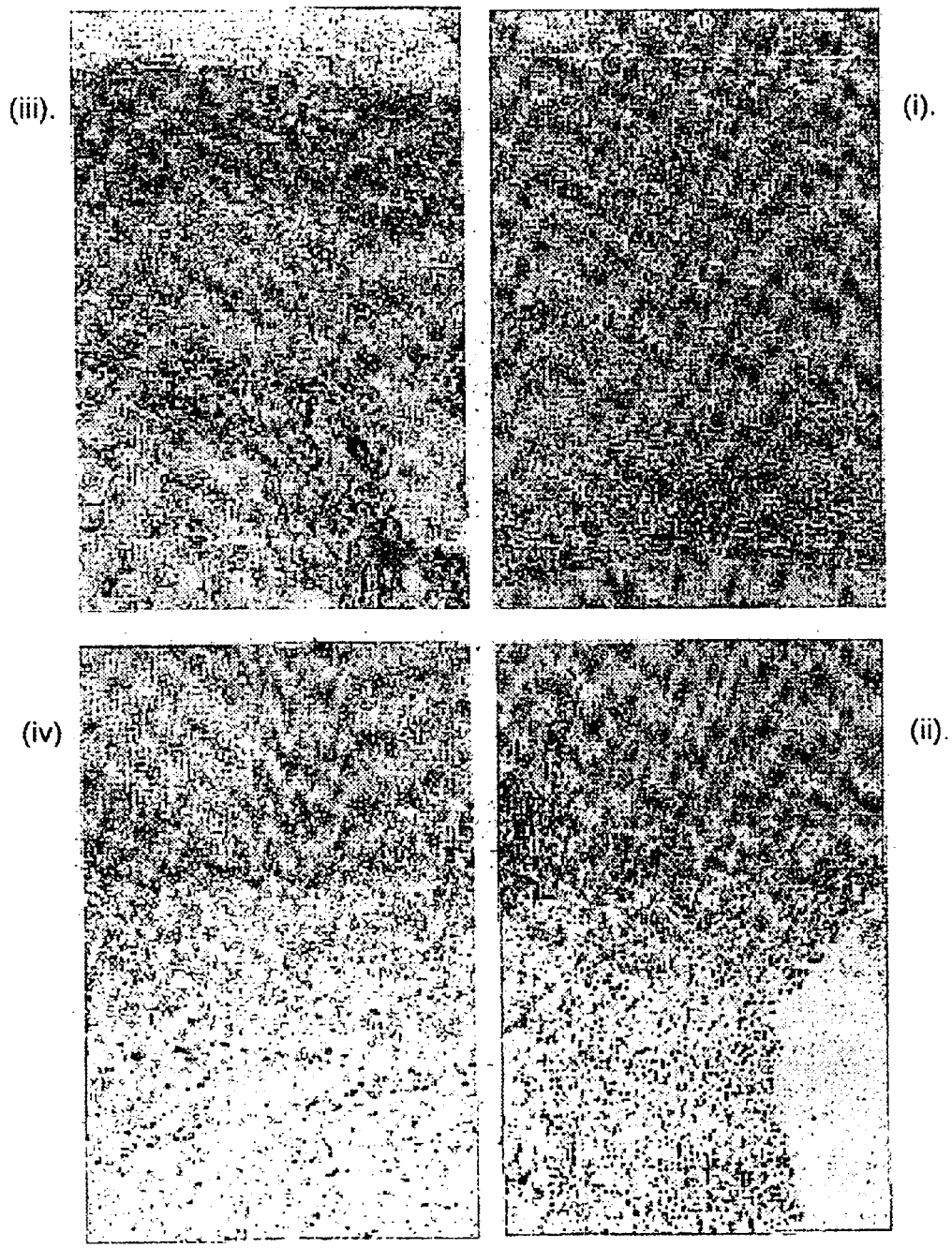
FIG. 6h shows immunostaining of Egr-1 protein in vessel wall pre and post injury.

Egr-1 activation of three growth factors was analysed by ELISA assay of cell supernatants. VEGF (FIG. 6e.), HGF (FIG. 6f.) and PDGF-AB (FIG. 6g.) production were all increased as a consequence of Egr-1 activation. There was a dose response of activation and an inverse dose response above a certain [Egr-1] DNA concentration as shown previously in Example 3.

6.3 Conclusion

Egr-1 protein is expressed in SMC following transfection of a CMV Egr-1 DNA. Transfection of Egr-1 increases the production/secretion of SMC derived PDGF, HGF and VEGF.

Example 7

EGR-1 Promoter Sequence

The human Egr-1 promoter fragment spanning nt. −674 to +12 was synthesised by PCR in a reaction containing 0.5 pg of human placental genomic DNA as a template, 0.4 mM of dATP, dCTP, dGTP and dTTP, 25 pmoles of the forward primer of SEQ ID NO:5 (5'-GGC CAC GCG TCG TCG GTT CGC TCT CAC GGT CCC-3', Mlu I restriction site is underlined), 25 pmoles of the reverse primer of SEQ ID NO:6 (5'-GCA GCT CGA GGC TGG ATC TCT CGC GAC TCC-3', Xho I restriction site is underlined) and Vent DNA polymerase (NEB). The PCR fragment was cut with Mlu I and Xho I, agarose gel-purified and cloned between the Mlu i and Xho I sites in the multiple cloning site of the vector pGL3 basic (Promega).

The full sequence has now been derived allowing completion of 'gaps' within the published sequence. This is shown in FIG. 7, where the complete sequence as derived by the inventors (GW SEQ) is compared with the previously published sequence (ON SEQ). This promoter sequence is functional and has been investigated in studies of shear stress on endothelial cells.

An important difference between the published sequence of the human Egr-1 promoter and the sequence which we describe (FIG. 8), lies in two previously unrecognised SREs. While the sequence of SRE 5 and SRE 1 as published do not bind serum response factor (SRF) and are not functional (Nurrish SJ, Treisman R, Mol Cell Biol 1995, 15(8): 4076–85), we have found that they are in agreement with the SRE consensus sequence (FIG. 7).

We have concentrated on SRE5. The novel SRE 5 with its associated Ets transcription factor binding sites was synthesised as a double stranded oligonucleotide and inserted into the Nhe I site upstream of a SV40 minimal promoter vector (pSV40). SRE5 (SEQ ID NOS:7–8) has the sequence:
A G G C T G C G A C C C G G A A A T G
CCATATAAGAAGCAGGAAGGATCCCCCCGCCGG
C G A C G C T G G G C C T T T A C
GGTATATTCTTCGTCCTTCCTAGGGGGGCGGCCGA The 2 Ets sites are bold, the SRE is underlined. The overhang AG is used to clone into the partially filled Nhe site of pGLE promoter.

The resulting reporter plasmid pSVSRE5 was transiently transfected into HeLa cells together with plasmids pFA-dbd (construct encoding the Gal4 DNA binding domain (dbd) ) or pFA-MEK1 (construct encoding a fusion protein of the Gal4 DNA binding domain (dbd) and the kinase domain of the MAP kinase kinase MEK1). The Gal4-MEK1 fusion protein is constitutively active and phosphorylates Elk1 and SRF, bound to SRE5.

The results shown in FIG. 10 show that the isolated SRE5 sequence is activated 3-fold by the presence of MEK1, while the SV40 promoter shows only minimal activation.

The results indicate that the novel SRE5 is functional.

We claim:

1. A method of treating wounds in a mammal, which method comprises administration of a nucleic acid molecule to a wound site wherein said nucleic acid molecule comprises a sequence encoding an Egr-1 transcription factor polypeptide or biologically active fragment thereof operatively linked to a nucleic acid sequence which controls expression and said nucleic acid molecule is in a vector.

2. A method of treating wounds in a mammal, which method comprises administration of a cell to a wound site wherein said cell comprises a nucleic acid molecule comprising a sequence encoding an Egr-1 transcription factor polypeptide or biologically active fragment thereof operatively linked to a nucleic acid sequence which controls expression and said nucleic acid molecule is in a vector.

3. A method of treating wounds in a mammal, which method comprises administration of a mammalian expression vector to a wound site wherein said mammalian expression vector comprises a nucleic acid molecule comprising a sequence encoding an Egr-1 transcription factor polypeptide or biologically active fragment thereof operatively linked to a nucleic acid sequence which controls expression.

* * * * *